United States Patent
Pollack

(10) Patent No.: US 9,863,913 B2
(45) Date of Patent: Jan. 9, 2018

(54) DIGITAL MICROFLUIDICS CARTRIDGE AND SYSTEM FOR OPERATING A FLOW CELL

(71) Applicant: ADVANCED LIQUID LOGIC, INC., San Diego, CA (US)

(72) Inventor: Michael G. Pollack, San Diego, CA (US)

(73) Assignee: Advanced Liquid Logic, Inc., San Diego, CA (US)

(*) Notice: Subject to any disclaimer, the term of this patent is extended or adjusted under 35 U.S.C. 154(b) by 173 days.

(21) Appl. No.: 14/428,219

(22) PCT Filed: Oct. 14, 2013

(86) PCT No.: PCT/US2013/064797
§ 371 (c)(1),
(2) Date: Mar. 13, 2015

(87) PCT Pub. No.: WO2014/062551
PCT Pub. Date: Apr. 24, 2014

(65) Prior Publication Data
US 2015/0212043 A1 Jul. 30, 2015

Related U.S. Application Data

(60) Provisional application No. 61/714,002, filed on Oct. 15, 2012, provisional application No. 61/714,484, (Continued)

(51) Int. Cl.
G01N 27/447 (2006.01)
B01L 3/00 (2006.01)
B01L 3/02 (2006.01)

(52) U.S. Cl.
CPC .. *G01N 27/44791* (2013.01); *B01L 3/502792* (2013.01); *G01N 27/44743* (2013.01);
(Continued)

(58) Field of Classification Search
CPC .............. G01N 27/44782; B01L 3/502784
See application file for complete search history.

(56) References Cited

U.S. PATENT DOCUMENTS 4,636,785 A 1/1987 Le Pesant
5,181,016 A 1/1993 Lee et al.
(Continued)

FOREIGN PATENT DOCUMENTS

JP 2006317364 A 11/2006
JP 2006329899 A 12/2006
(Continued)

OTHER PUBLICATIONS

Bali et al., "Comparison of methods for the analysis of lysosomal enzyme activities in quality control dried blood spot specimens", 2013 International Conference on Inborn Errors of Metabolism (IEM): India. New Delhi, India. Poster presentation, abstract published in conference proceedings, Apr. 4-7, 2013.
(Continued)

*Primary Examiner* — J. Christopher Ball
(74) *Attorney, Agent, or Firm* — Illumina, Inc.

(57) ABSTRACT

A liquid handling system for supplying liquids to a flow cell (FC). The system may include a droplet actuator cartridge, wherein the droplet actuator and a flow cell are fluidly coupled to, or situated within, a droplet operations gap of the droplet actuator.

20 Claims, 12 Drawing Sheets

Related U.S. Application Data filed on Oct. 16, 2012, provisional application No. 61/723,596, filed on Nov. 7, 2012.

(52) U.S. Cl.
CPC ........ B01L 3/0241 (2013.01); B01L 2300/088 (2013.01); B01L 2300/0816 (2013.01); B01L 2300/0867 (2013.01); B01L 2300/0883 (2013.01); B01L 2300/1827 (2013.01); B01L 2400/043 (2013.01); B01L 2400/0427 (2013.01); B01L 2400/0457 (2013.01)

(56) References Cited

U.S. PATENT DOCUMENTS

| | | |
|---|---|---|
| 5,486,337 A | 1/1996 | Ohkawa et al. |
| 6,063,339 A | 5/2000 | Tisone et al. |
| 6,130,098 A | 10/2000 | Handique et al. |
| 6,294,063 B1 | 9/2001 | Becker et al. |
| 6,565,727 B1 | 5/2003 | Shenderov |
| 6,773,566 B2 | 8/2004 | Shenderov |
| 6,790,011 B1 | 9/2004 | Le Pesant et al. |
| 6,911,132 B2 | 6/2005 | Pamula et al. |
| 6,924,792 B1 | 8/2005 | Jessop |
| 6,977,033 B2 | 12/2005 | Becker et al. |
| 6,989,234 B2 | 1/2006 | Kolar et al. |
| 7,052,244 B2 | 5/2006 | Fouillet et al. |
| 7,163,612 B2 | 1/2007 | Sterling et al. |
| 7,211,223 B2 | 5/2007 | Fouillet et al. |
| 7,255,780 B2 | 8/2007 | Shenderov |
| 7,328,979 B2 | 2/2008 | Decre et al. |
| 7,329,545 B2 | 2/2008 | Pamula et al. |
| 7,439,014 B2 | 10/2008 | Pamula et al. |
| 7,458,661 B2 | 12/2008 | Kim et al. |
| 7,531,072 B2 | 5/2009 | Roux et al. |
| 7,547,380 B2 | 6/2009 | Velev |
| 7,569,129 B2 | 8/2009 | Pamula et al. |
| 7,641,779 B2 | 1/2010 | Becker et al. |
| 7,727,466 B2 | 6/2010 | Meathrel et al. |
| 7,727,723 B2 | 6/2010 | Pollack et al. |
| 7,759,132 B2 | 7/2010 | Pollack et al. |
| 7,763,471 B2 | 7/2010 | Pamula et al. |
| 7,815,871 B2 | 10/2010 | Pamula et al. |
| 7,816,121 B2 | 10/2010 | Pollack et al. |
| 7,822,510 B2 | 10/2010 | Paik et al. |
| 7,851,184 B2 | 12/2010 | Pollack et al. |
| 7,875,160 B2 | 1/2011 | Jary |
| 7,901,947 B2 | 3/2011 | Pollack et al. |
| 7,919,330 B2 | 4/2011 | De Guzman et al. |
| 7,922,886 B2 | 4/2011 | Fouillet et al. |
| 7,939,021 B2 | 5/2011 | Smith et al. |
| 7,943,030 B2 | 5/2011 | Shenderov |
| 7,989,056 B2 | 8/2011 | Plissonier et al. |
| 7,998,436 B2 | 8/2011 | Pollack |
| 8,007,739 B2 | 8/2011 | Pollack et al. |
| 8,041,463 B2 | 10/2011 | Pollack et al. |
| 8,048,628 B2 | 11/2011 | Pollack et al. |
| 8,075,754 B2 | 12/2011 | Sauter-Starace et al. |
| 8,088,578 B2 | 1/2012 | Hua et al. |
| 8,093,062 B2 | 1/2012 | Winger et al. |
| 8,093,064 B2 | 1/2012 | Shah et al. |
| 8,137,917 B2 | 3/2012 | Pollack et al. |
| 8,147,668 B2 | 4/2012 | Pollack et al. |
| 8,202,686 B2 | 6/2012 | Pamula et al. |
| 8,208,146 B2 | 6/2012 | Srinivasan et al. |
| 8,221,605 B2 | 7/2012 | Pollack et al. |
| 8,236,156 B2 | 8/2012 | Sarrut et al. |
| 8,268,246 B2 | 9/2012 | Srinivasan et al. |
| 8,287,711 B2 | 10/2012 | Pollack et al. |
| 8,304,253 B2 | 11/2012 | Yi et al. |
| 8,313,698 B2 | 11/2012 | Pollack et al. |
| 8,317,990 B2 | 11/2012 | Pamula et al. |
| 8,342,207 B2 | 1/2013 | Raccurt et al. |
| 8,349,276 B2 | 1/2013 | Pamula et al. |
| 8,364,315 B2 | 1/2013 | Sturmer et al. |
| 8,388,909 B2 | 3/2013 | Pollack et al. |
| 8,389,297 B2 | 3/2013 | Pamula et al. |
| 8,394,249 B2 | 3/2013 | Pollack et al. |
| 8,394,641 B2 | 3/2013 | Winger |
| 8,426,213 B2 | 4/2013 | Eckhardt et al. |
| 8,440,392 B2 | 5/2013 | Pamula et al. |
| 8,444,836 B2 | 5/2013 | Fouillet et al. |
| 2002/0005354 A1 | 1/2002 | Spence et al. |
| 2002/0036139 A1 | 3/2002 | Becker et al. |
| 2002/0043463 A1 | 4/2002 | Shenderov |
| 2002/0058332 A1 | 5/2002 | Quake et al. |
| 2002/0143437 A1 | 10/2002 | Handique et al. |
| 2003/0164295 A1 | 9/2003 | Sterling |
| 2003/0183525 A1 | 10/2003 | Elrod et al. |
| 2003/0205632 A1 | 11/2003 | Kim et al. |
| 2004/0031688 A1 | 2/2004 | Shenderov |
| 2004/0055891 A1 | 3/2004 | Pamula et al. |
| 2004/0058450 A1 | 3/2004 | Pamula et al. |
| 2004/0231987 A1 | 11/2004 | Sterling et al. |
| 2006/0021875 A1 | 2/2006 | Griffith et al. |
| 2006/0054503 A1 | 3/2006 | Pamula et al. |
| 2006/0164490 A1 | 7/2006 | Kim et al. |
| 2006/0194331 A1 | 8/2006 | Pamula et al. |
| 2006/0231398 A1 | 10/2006 | Sarrut et al. |
| 2007/0023292 A1 | 2/2007 | Kim et al. |
| 2007/0037294 A1 | 2/2007 | Pamula et al. |
| 2007/0045117 A1 | 3/2007 | Pamula et al. |
| 2007/0064990 A1 | 3/2007 | Roth |
| 2007/0086927 A1 | 4/2007 | Natarajan et al. |
| 2007/0207513 A1 | 9/2007 | Sorensen et al. |
| 2007/0217956 A1 | 9/2007 | Pamula et al. |
| 2007/0241068 A1 | 10/2007 | Pamula et al. |
| 2007/0242105 A1 | 10/2007 | Srinivasan et al. |
| 2007/0242111 A1 | 10/2007 | Pamula et al. |
| 2007/0243634 A1 | 10/2007 | Pamula et al. |
| 2007/0267294 A1 | 11/2007 | Shenderov |
| 2007/0275415 A1 | 11/2007 | Srinivasan et al. |
| 2008/0006535 A1 | 1/2008 | Paik et al. |
| 2008/0038810 A1 | 2/2008 | Pollack et al. |
| 2008/0044893 A1 | 2/2008 | Pollack et al. |
| 2008/0044914 A1 | 2/2008 | Pamula et al. |
| 2008/0050834 A1 | 2/2008 | Pamula et al. |
| 2008/0053205 A1 | 3/2008 | Pollack et al. |
| 2008/0105549 A1 | 5/2008 | Pamela et al. |
| 2008/0124252 A1 | 5/2008 | Marchand et al. |
| 2008/0142376 A1 | 6/2008 | Fouillet et al. |
| 2008/0151240 A1 | 6/2008 | Roth |
| 2008/0210558 A1 | 9/2008 | Sauter-Starace et al. |
| 2008/0247920 A1 | 10/2008 | Pollack et al. |
| 2008/0264797 A1 | 10/2008 | Pamula et al. |
| 2008/0274513 A1 | 11/2008 | Shenderov et al. |
| 2008/0281471 A1 | 11/2008 | Smith et al. |
| 2008/0283414 A1 | 11/2008 | Monroe et al. |
| 2008/0302431 A1 | 12/2008 | Marchand et al. |
| 2008/0305481 A1 | 12/2008 | Whitman et al. |
| 2009/0014394 A1 | 1/2009 | Yi et al. |
| 2009/0042319 A1 | 2/2009 | De Guzman et al. |
| 2009/0127123 A1 | 5/2009 | Raccurt et al. |
| 2009/0134027 A1 | 5/2009 | Jary |
| 2009/0142564 A1 | 6/2009 | Plissonnier et al. |
| 2009/0155902 A1 | 6/2009 | Pollack et al. |
| 2009/0192044 A1 | 7/2009 | Fouillet |
| 2009/0260988 A1 | 10/2009 | Pamula et al. |
| 2009/0263834 A1 | 10/2009 | Sista et al. |
| 2009/0280251 A1 | 11/2009 | De Guzman et al. |
| 2009/0280475 A1 | 11/2009 | Pollack et al. |
| 2009/0280476 A1 | 11/2009 | Srinivasan et al. |
| 2009/0283407 A1 | 11/2009 | Shah et al. |
| 2009/0288710 A1 | 11/2009 | Viovy et al. |
| 2009/0291433 A1 | 11/2009 | Pollack et al. |
| 2009/0304944 A1 | 12/2009 | Sudarsan et al. |
| 2009/0311713 A1 | 12/2009 | Pollack et al. |
| 2009/0321262 A1 | 12/2009 | Adachi et al. |
| 2010/0025242 A1 | 2/2010 | Pamula et al. |
| 2010/0025250 A1 | 2/2010 | Pamula et al. |
| 2010/0028920 A1 | 2/2010 | Eckhardt |
| 2010/0032293 A1 | 2/2010 | Pollack et al. |
| 2010/0041086 A1 | 2/2010 | Pamula et al. |
| 2010/0048410 A1 | 2/2010 | Shenderov et al. |

(56) References Cited

U.S. PATENT DOCUMENTS

| | | |
|---|---|---|
| 2010/0062508 A1 | 3/2010 | Pamula et al. |
| 2010/0068764 A1 | 3/2010 | Sista et al. |
| 2010/0087012 A1 | 4/2010 | Shenderov et al. |
| 2010/0096266 A1 | 4/2010 | Kim et al. |
| 2010/0116640 A1 | 5/2010 | Pamula et al. |
| 2010/0118307 A1 | 5/2010 | Srinivasan et al. |
| 2010/0120130 A1 | 5/2010 | Srinivasan et al. |
| 2010/0126860 A1 | 5/2010 | Srinivasan et al. |
| 2010/0130369 A1 | 5/2010 | Shenderov et al. |
| 2010/0140093 A1 | 6/2010 | Pamula et al. |
| 2010/0143963 A1 | 6/2010 | Pollack |
| 2010/0151439 A1 | 6/2010 | Pamula et al. |
| 2010/0190263 A1 | 7/2010 | Srinivasan et al. |
| 2010/0194408 A1 | 8/2010 | Sturmer et al. |
| 2010/0221713 A1 | 9/2010 | Pollack et al. |
| 2010/0236927 A1 | 9/2010 | Pope et al. |
| 2010/0236928 A1 | 9/2010 | Srinivasan et al. |
| 2010/0236929 A1 | 9/2010 | Pollack et al. |
| 2010/0258441 A1 | 10/2010 | Sista et al. |
| 2010/0270156 A1 | 10/2010 | Srinivasan et al. |
| 2010/0279374 A1 | 11/2010 | Sista et al. |
| 2010/0282608 A1 | 11/2010 | Srinivasan et al. |
| 2010/0282609 A1 | 11/2010 | Pollack et al. |
| 2010/0307917 A1 | 12/2010 | Srinivasan et al. |
| 2010/0320088 A1 | 12/2010 | Fouillet et al. |
| 2010/0323405 A1 | 12/2010 | Pollack et al. |
| 2011/0076692 A1 | 3/2011 | Sista et al. |
| 2011/0086377 A1 | 4/2011 | Thwar et al. |
| 2011/0091989 A1 | 4/2011 | Sista et al. |
| 2011/0097763 A1 | 4/2011 | Pollack et al. |
| 2011/0100823 A1 | 5/2011 | Pollack et al. |
| 2011/0104725 A1 | 5/2011 | Pamula et al. |
| 2011/0104747 A1 | 5/2011 | Pollack et al. |
| 2011/0104816 A1 | 5/2011 | Pollack et al. |
| 2011/0114490 A1 | 5/2011 | Pamula et al. |
| 2011/0118132 A1 | 5/2011 | Winger et al. |
| 2011/0147215 A1 | 6/2011 | Fuchs et al. |
| 2011/0180571 A1 | 7/2011 | Srinivasan et al. |
| 2011/0186433 A1 | 8/2011 | Pollack et al. |
| 2011/0203930 A1 | 8/2011 | Pamula et al. |
| 2011/0209998 A1 | 9/2011 | Shenderov |
| 2011/0213499 A1 | 9/2011 | Sturmer et al. |
| 2011/0303542 A1 | 12/2011 | Srinivasan et al. |
| 2011/0311980 A1 | 12/2011 | Pollack et al. |
| 2012/0018306 A1 | 1/2012 | Srinivasan et al. |
| 2012/0044299 A1 | 2/2012 | Winger |
| 2012/0132528 A1 | 5/2012 | Shenderov et al. |
| 2012/0136147 A1 | 5/2012 | Winger |
| 2012/0165238 A1 | 6/2012 | Pamula et al. |
| 2013/0017544 A1 | 1/2013 | Eckhardt et al. |
| 2013/0018611 A1 | 1/2013 | Sturmer |
| 2013/0059366 A1 | 3/2013 | Pollack et al. |

FOREIGN PATENT DOCUMENTS

| | | | |
|---|---|---|---|
| JP | 2006329904 A | | 12/2006 |
| WO | 2000069565 A1 | | 11/2000 |
| WO | 2000073655 A1 | | 12/2000 |
| WO | 2004029585 A1 | | 4/2004 |
| WO | 2004030820 | | 4/2004 |
| WO | 2005047696 A1 | | 5/2005 |
| WO | 2006013303 A1 | | 2/2006 |
| WO | 2006070162 A1 | | 7/2006 |
| WO | 2006081558 | | 8/2006 |
| WO | 2006124458 A2 | | 11/2006 |
| WO | 2006127451 A2 | | 11/2006 |
| WO | 2006129486 A1 | | 12/2006 |
| WO | 2006132211 A1 | | 12/2006 |
| WO | 2006134307 A1 | | 12/2006 |
| WO | 2006138543 | | 12/2006 |
| WO | 2007003720 A1 | | 1/2007 |
| WO | 2007012638 A1 | | 2/2007 |
| WO | 2007033990 A1 | | 3/2007 |
| WO | 2007048111 | | 4/2007 |
| WO | 2007120240 A2 | | 10/2007 |
| WO | 2007120241 A2 | | 10/2007 |
| WO | 2007123908 A2 | | 11/2007 |
| WO | 2008051310 A2 | | 5/2008 |
| WO | 2008055256 A3 | | 5/2008 |
| WO | 2008068229 A1 | | 6/2008 |
| WO | 2008091848 A2 | | 7/2008 |
| WO | 2008098236 A2 | | 8/2008 |
| WO | 2008101194 A2 | | 8/2008 |
| WO | 2008106678 A1 | | 9/2008 |
| WO | 2008109664 A1 | | 9/2008 |
| WO | 2008112856 A1 | | 9/2008 |
| WO | 2008116209 A1 | | 9/2008 |
| WO | 2008116221 A1 | | 9/2008 |
| WO | 2008118831 A2 | | 10/2008 |
| WO | 2008124846 A2 | | 10/2008 |
| WO | 2008131420 A2 | | 10/2008 |
| WO | 2008134153 A1 | | 11/2008 |
| WO | 2009002920 A1 | | 12/2008 |
| WO | 2009003184 A1 | | 12/2008 |
| WO | 2009011952 A1 | | 1/2009 |
| WO | 2009021173 A1 | | 2/2009 |
| WO | 2009021233 A2 | | 2/2009 |
| WO | 2009026339 A2 | | 2/2009 |
| WO | 2009029561 A2 | | 3/2009 |
| WO | 2009032863 A2 | | 3/2009 |
| WO | 2009052095 A1 | | 4/2009 |
| WO | 2009052123 A2 | | 4/2009 |
| WO | 2009052321 A2 | | 4/2009 |
| WO | 2009052345 A1 | | 4/2009 |
| WO | 2009052348 A2 | | 4/2009 |
| WO | 2009076414 | | 6/2009 |
| WO | 2009086403 A2 | | 7/2009 |
| WO | 2009111769 A2 | | 9/2009 |
| WO | 2009135205 A2 | | 11/2009 |
| WO | 2009137415 A2 | | 11/2009 |
| WO | 2009140373 A2 | | 11/2009 |
| WO | 2009140671 A2 | | 11/2009 |
| WO | 2010004014 A1 | | 1/2010 |
| WO | 2010006166 A2 | | 1/2010 |
| WO | 2010009463 A2 | | 1/2010 |
| WO | 2010019782 A2 | | 2/2010 |
| WO | 2010027894 A2 | | 3/2010 |
| WO | 2010042637 A2 | | 4/2010 |
| WO | WO 2010040227 A1 * | 4/2010 | ........ B01L 3/502715 |
| WO | 2010077859 A3 | | 7/2010 |
| WO | 2011002957 A2 | | 1/2011 |
| WO | 2011020011 A2 | | 2/2011 |
| WO | 2011057197 A2 | | 5/2011 |
| WO | 2011084703 A2 | | 7/2011 |
| WO | 2011126892 A2 | | 10/2011 |
| WO | 2012009320 A2 | | 1/2012 |
| WO | 2012012090 A2 | | 1/2012 |
| WO | 2012037308 A2 | | 3/2012 |
| WO | 2012068055 A3 | | 5/2012 |
| WO | 2013009927 A3 | | 1/2013 |

OTHER PUBLICATIONS

Bali et al., "Comparison of Methods for the Analysis of Lysosomal Enzyme Activities in Quality Control Dried Blood Spot Specimens", LSD World Meeting, Orlando, FL, poster presented, Feb. 12-15, 2013.

Bali et al., "Digital microfluidics: a single multiplex platform for rapid newborn screening", 2013 International Conference on Inborn Errors of Metabolism (IEM): India, New Delhi, India, oral presentation,poster presentation, abstract published in conf. proceedings, Apr. 4-7, 2013.

Benton et al., "Library Preparation Method 1 DNA Library Construction for Illumine SBS Sequencing Platforms using NEBNext® Library Preparation Reagents", Application Note, NuGEN, 2011.

Boles et al., "Droplet-Based Pyrosequencing Using Digital Microfluidics", Analytical Chemistry, vol. 83, Sep. 2011, 8439-47.

Bottausci et al., "Fully Integrated EWOD Based Bio-Analysis Device", Labautomation 2011, Palm Springs Convention Center, Palm Springs, CA, USA; Abstract in Proceedings on line, poster distributed, Jan. 29-Feb. 2, 2011.

(56) References Cited

OTHER PUBLICATIONS

Burde et al., "Digital Microfluidic Rapid HIV Point-of-Care Diagnostic Device for Resource Limited Settings", Workshop on TB and HIV Diagnostics, Silver Spring, MD. (Poster, copies distributed to attendees.) http://www.blsmeetings.net/TB-HIV-Dx-Wkshop/index.cfm, Jun. 28, 2011.

Burton et al., "Diagnosis of Fabry and Gaucher diseases from the Pilot Screening of Newborns for Lysosomal Storage Disorders in Illinois", APHL Newborn Screening and Genetic Testing Symposium, San Diego, 2011.

Chakrabarty, "Automated Design of Microfluidics-Based Biochips: connecting Biochemistry of Electronics CAD", IEEE International Conference on Computer Design, San Jose, CA, Oct. 1-4, 2006, 93-100.

Chakrabarty et al., "Design Automation Challenges for Microfluidics-Based Biochips", DTIP of MEMS & MOEMS, Montreux, Switzerland, Jun. 1-3, 2005.

Chakrabarty et al., "Design Automation for Microfluidics-Based Biochips", ACM Journal on Engineering Technologies in Computing Systems , 1(3), Oct. 2005, 186-223.

Chakrabarty, "Design, Testing, and Applications of Digital Microfluidics-Based Biochips", Proceedings of the 18th International Conf. on VLSI held jointly with 4th International Conf. on Embedded Systems Design (VLSID'05), IEEE, Jan. 3-7, 2005.

Chen et al., "Development of Mesoscale Actuator Device with Micro Interlocking Mechanism", J. Intelligent Material Systems and Structures, vol. 9, No. 4, Jun. 1998, pp. 449-457.

Chen et al., "Mesoscale Actuator Device with Micro Interlocking Mechanism", Proc. IEEE Micro Electro Mechanical Systems Workshop, Heidelberg, Germany, Jan. 1998, pp. 384-389.

Chen et al., "Mesoscale Actuator Device: Micro Interlocking Mechanism to Transfer Macro Load", Sensors and Actuators, vol. 73, Issues 1-2, Mar. 1999, pp. 30-36.

Cohen, "Automated Multianalyte Screening Tool for Classification of Forensic Samples", NIJ conference 2012, http://www.nij.gov/nij/events/nij_conference/2012/nij-2012-program-book.pdf, 2012.

Cohen, "Low Cost Sample-to-Sequence Device for Human & Pathogen ID", Integrating Sample Prep, Baltimore, MD, Oct. 18, 2012.

Cohen, "Digital Microfluidic Sample Prep & Bioanalytical Systems", BioDot Workshop: From R&D to Quantitative IVDs, Irvine, CA, Apr. 24, 2012.

Cotten et al., "Digital Microfluidics: a novel platform for multiplexed detection of lysosomal storage diseases", Abstract # 3747.9. Pediatric Academic Society Conference, 2008.

Delapierre et al., "SmartDrop: An Integrated System from Sample Collection to Result using real-time PCR", 4th National Bio-Threat Conference, Dec. 7-9, 2010, New Orleans, LA, USA; Abstract in Proceedings, Poster presented at conference.

Delattre, Movie in news on TF1 (at 12'37" Cyril Delattre) http://videos.tf1.fr/jt-we/zoom-sur-grenoble-6071525.html, 2009, (English translation of audio).

Delattre, Movie in talk show "C Dans l'air" (at 24" Cyril Delattre), http://www.france5.fr/c-dans-l-air/sante/bientot-vous-ne-serez-plus-malade-31721, 2009, (English translation of audio).

Delattre, Movie on Web TV—Cite des sciences (at 3'26" Cyril Delattre), http://www.universcience.tv/video-laboratoire-de-poche-793.html, 2009, (English translation of audio).

Delattre et al., "Macro to microfluidics system for biological environmental monitoring", Biosensors and Bioelectronics, vol. 36, Issue 1, 2012, Available online, Apr. 27, 2012, 230-235.

Delattre et al., "SmartDrop: an integrated system from sample preparation to analysis using real-time PCR", 10th International Symposium on Protection against Chemical and Biological Warfare Agents; Stockholm, Sweden; poster, Jun. 10, 2010.

Delattre et al., "SmartDrop: An integrated system from sample preparation to analysis using real-time PCR", 10th International Symposium on Protection against Chemical and Biological Warfare Agents; Stockholm, Sweden; Abstract,paper,, Jun. 8-11, 2010.

Delattre et al., "Towards an industrial fabrication process for electrowetting chip using standard MEMS Technology", µTAS2008, San Diego; poster presented, Oct. 15, 2008.

Delattre et al., "Towards an industrial fabrication process for electrowetting chip using standard MEMS Technology", µTAS2008, San Diego; Abstract in proceedings, Oct. 13-16, 2008, 1696-1698.

Dewey, "Towards a Visual Modeling Approach to Designing Microelectromechanical System Transducers", Journal of Micromechanics and Microengineering, vol. 9, Dec. 1999, 332-340.

Dewey et al., "Visual modeling and design of microelectromechanical system tansducers", Microelectronics Journal, vol. 32, Apr. 2001, 373-381.

Eckhardt et al., "Development and validation of a single-step fluorometric assay for Hunter syndrome", APHL Newborn Screening and Genetic Testing Symposium, San Diego, 2011.

Emani et al., "Novel microfluidic platform for automated lab-on-chip testing of hypercoagulability panel", Blood Coagulation and Fibrinolysis, vol. 23(8), 2012, 760-8.

Emani et al., "Novel Microfluidic Platform for Point of Care Hypercoagulability Panel Testing", Circulation, vol. 122, 2010, A14693.

Fair et al., "A Micro- Watt Metal-Insulator-Solution-Transport (MIST) Device for Scalable Digital Bio-Microfluidic Systems", IEEE IEDM Technical Digest, 2001, 16.4.1-4.

Fair et al., "Advances in droplet-based bio lab-on-a-chip", BioChips 2003, Boston, 2003.

Fair et al., "Bead-Based and Solution-Based Assays Performed on a Digital Microfluidic Platform", Biomedical Engineering Society (BMES) Fall Meeting, Baltimore, MD, Oct. 1, 2005.

Fair, "Biomedical Applications of Electrowetting Systems", 5th International Electrowetting Workshop, Rochester, NY, May 31, 2006.

Fair et al., "Chemical and Biological Applications of Digital-Microfluidic Devices", IEEE Design & Test of Computers, vol. 24(1), Jan.-Feb. 2007, 10-24.

Fair et al., "Chemical and biological pathogen detection in a digital microfluidic platform", DARPA Workshop on Microfluidic Analyzers for DoD and National Security Applications, Keystone, CO, 2006.

Fair, "Digital microfluidics: is a true lab-on-a-chip possible?", Microfluid Nanofluid, vol. 3, Mar. 8, 2007, 245-281.

Fair, "Droplet-based microfluidic Genome sequencing", NHGRI PI's meeting, Boston, 2005.

Fair et al., "Electrowetting-based On-Chip Sample Processing for Integrated Microfluidics", IEEE Inter. Electron Devices Meeting (IEDM), 2003, 32.5.1-32.5.4.

Fair et al., "Integrated chemical/biochemical sample collection, pre-concentration, and analysis on a digital microfluidic lab-on-a-chip platform", Lab-on-a-Chip: Platforms, Devices, and Applications, Conf. 5591, SPIE Optics East, Philadelphia, Oct. 25-28, 2004.

Fair, "Scaling of Digital Microfluidic Devices for Picoliter Applications", The 6th International Electrowetting Meeting, Aug. 20-22, 2008, p. 14.

Fouillet, "Bio-Protocol Integration in Digital Microfluidic Chips", The 6th International Electrowetting Meeting, Aug. 20-22, 2008, p. 15.

Fouillet et al., "Design and Validation of a Complex Generic Fluidic Microprocessor Based on EWOD Droplet for Biological Applications", 9th International Conference on Miniaturized Systems for Chem and Life Sciences, Boston, MA, Oct. 9-13, 2005, 58-60.

Fouillet et al., "Digital microfluidic design and optimization of classic and new fluidic functions for lab on a chip systems", Microfluid Nanofluid, vol. 4, 2008, 159-165.

Graham et al., "Development of Quality Control Spots for Lysosomal Storage Disorders under cGMP", APHL Newborn Screening and Genetic Testing Symposium, San Diego, 2011.

Graham et al., "Fluorometric reagent kits for screening Lysosomal Storage Disorders: One year stability evaluation and shelf-life recommendations", Extended abstract from the 2013 APHL Newborn Screening and Genetic Testing Symposium and the International Society for Neonatal Screening, Atlanta, GA.

(56) References Cited

OTHER PUBLICATIONS

Graham et al., "Fluorometric reagent kits for screening Lysosomal Storage Disorders: One year stability evaluation and shelf-life recommendations", 2013 APHL Newborn Screening and Genetic Testing Symposium and the International Society for Neonatal Screening,Atlanta, GA.Poster presented, abstract published in conference proceedings, May 5-10, 2013.

Hua et al., "Multiplexed real-time polymerase chain reaction on a digital microfluidic platform", Analytical Chemistry, vol. 82, No. 6, Mar. 15, 2010, Published on Web, Feb. 12, 2010, 2310-2316.

Hua et al., "Rapid Detection of Methicillin-Resistant *Staphylococcus aureus* (MRSA) Using Digital Microfluidics", 12th Intl Conference on Miniaturized Systems for Chemistry and Life Sciences, Proc. µTAS, Oct. 12-16, 2008.

Jary et al., "Development of complete analytical system for Environment and homeland security", 14th International Conference on Biodetection Technologies 2009, Technological Responses to Biological Threats, Baltimore, MD; Abstract in Proceedings, poster distributed at conference, Jun. 25-26, 2009, 663.

Jary et al., "SmartDrop, Microfluidics for Biology", Forum 4i 2009, Grenoble, France; Flyer distributed at booth, May 14, 2009.

Jun et al., "Valveless Pumping using Traversing Vapor Bubbles in Microchannels", J. Applied Physics, vol. 83, No. 11, Jun. 1998, pp. 5658-5664.

Kim et al., "MEMS Devices Based on the Use of Surface Tension", Proc. Int. Semiconductor Device Research Symposium (ISDRS'99), Charlottesville, VA, Dec. 1999, pp. 481-484.

Kim, "Microelectromechanical Systems (MEMS) at the UCLA Micromanufacturing Lab", Dig. Papers, Int. Microprocesses and Nanotechnology Conf. (MNC'98), Kyungju, Korea, Jul. 1998, pp. 54-55.

Kim et al., "Micromachines Driven by Surface Tension", AIAA 99-3800, 30th AIAA Fluid Dynamics Conference, Norfolk, VA, (Invited lecture), Jun. 1999, pp. 1-6.

Kleinert et al., "Digital microfluidic platform for newborn screening using whole blood in hospital settings for hyperbilirubinemia", Extended abstract from the 2013 APHL Newborn Screening and Genetic Testing Symposium and the International Society for Neonatal Screening.

Kleinert et al., "Digital microfluidic platform for newborn screening using whole blood in hospital settings for hyperbilirubinemia", 2013 APHL Newborn Screening and Genetic Testing Symposium and the International Society for Neonatal Screening, Atlanta, GA, Poster presented, abstract published in proceedings, May 5-10, 2013.

Kleinert et al., "Dynamics and Stability of Oil Films During Droplet Transport by Electrowetting", 86th ACS Colloid & Surface Science Symposium, Abstract, Jun. 13, 2012.

Kleinert et al., "Dynamics and Stability of Oil Films During Droplet Transport by Electrowetting", 86th ACS Colloid & Surface Science Symposium, Presentation, Jun. 13, 2012.

Kleinert et al., "Dynamics and stability of oil films during droplet transport by electrowetting", 8th International Meeting on Electrowetting, Athens, Greece, Jun. 21-23, 2012.

Kleinert et al., "Electric Field Assisted Convective Assembly of Colloidal Crystal Coatings", Symposium MM: Evaporative Self Assembly of Polymers, Nanoparticles, and DNA, 2010 MRS Spring Meeting, San Francisco, CA., Apr. 6-8, 2010.

Kleinert et al., "Electric Field-Assisted Convective Assembly of Large-Domain Colloidal Crystals", The 82nd Colloid & Surface Science Symposium, ACS Division of Colloid & Surface Science, North Carolina State University, Raleigh, NC. www.colloids2008.org., Jun. 15-18, 2008.

Kleinert, "Electric-Field-Assisted Convective Assembly of Colloidal Crystal Coatings", Langmuir, vol. 26(12), May 13, 2010, 10380-10385.

Kleinert et al., "Evaluation of a Digital Microfluidic Platform for Point of Care Newborn Screening of Hyperbilirubinemia, Congenital Hypothyroidism and G6PD Deficiency in Emerging Programs", Pediatric Academic Societies Annual Meeting, Washington, D.C, Abstract, http://www.abstracts2view.com/pas/., May 4-7, 2013.

Kleinert et al., "Evaluation of a Digital Microfluidic Platform for Point of Care Newborn Screening of Hyperbilirubinemia, Congenital Hypothyroidism and G6PD Deficiency in Emerging Programs", Pediatric Academic Societies Annual Meeting,Washington, D.C., Poster, May 4-7, 2013.

Kleinert, "Liquid Transport and Colloidal Self Assembly in Thin Wetting Films Driven by Electric Fields", PhD Dissertation, North Carolina State University, 2013.

Lee et al., "Microactuation by Continuous Electrowetting Phenomenon and Silicon Deep Rie Process", Proc. MEMS (DSC—vol. 66) ASME Int. Mechanical Engineering Congress and Exposition, Anaheim, CA, Nov. 1998, 475-480.

Lee et al., "Liquid Micromotor Driven by Continuous Electrowetting", Proc. IEEE Micro Electro Mechanical Systems Workshop, Heidelberg, Germany, Jan. 1998, pp. 538-543.

Lee et al., "Theory and Modeling of Continuous Electrowetting Microactuation", Proc. MEMS (MEMS—vol. 1), ASME Int. Mechanical Engineering Congress and Exposition, Nashville, TN, Nov. 1999, pp. 397-403.

Malk et al., "EWOD in coplanar electrode configurations", Proceedings of ASME 2010 3rd Joint US-European Fluids Engineering Summer Meeting and 8th International Conference on Nanochannels, Microchannels, and Minichannels, http://asmedl.org/getabs/servlet/GetabsServlet?prog=normal&id=ASMECP002010054501000239000000, Aug. 1-5, 2010.

Marchand et al., "Organic Synthesis in Soft Wall-Free Microreactors: Real-Time Monitoring of Fluorogenic Reactions", Analytical Chemistry, vol. 80, Jul. 2, 2008, 6051-6055.

Millington et al., "Applications of tandem mass spectrometry and microfluidics in newborn screening", Southeastern Regional Meeting of the American Chemical Society, Raleigh, North Carolina, 2012.

Millington et al., "Digital microfluidics: a future technology in the newborn screening laboratory", Seminars in Perinatology, vol. 34, Apr. 2010, 163-169.

Millington et al., "Digital Microfluidics: a novel platform for multiplexed detection of LSDs with potential for newborn screening", Association of Public Health Laboratories Annual Conference, San Antonio, TX, Nov. 4, 2008.

Millington et al., "Digital Microfluidics: A Novel Platform for Multiplexing Assays Used in Newborn Screening", Proceedings of the7th International and Latin American Congress. Oral Presentations. Rev Invest Clin; vol. 61 (Supl. 1), 2009, 21-33.

Mugele et al., "Electrowetting: from basics to applications", Institution of Physics Publishing, Journal of Physics: Condensed Matter, 2005, R705-R774.

Nuffer et al., "Sample-to-Sequence Analyzer for Human ID Applications", 23rd International Symposium for Human Identification, Nashville, TN. http://www.promega.com/~/media/files/resources/conference%20proceedings/ishi%2023/poster%20abstracts/32%20poster.pdf?la=en, Oct. 16-17, 2012.

Paik et al., "A digital-microfluidic approach to chip cooling", IEEE Design & Test of Computers, vol. 25, Jul. 2008, 372-381.

Paik et al., "Adaptive Cooling of Integrated Circuits Using Digital Microfluidics", IEEE Transactions on VLSI, vol. 16, No. 4, 2008, 432-443.

Paik et al., "Adaptive Cooling of Integrated Circuits Using Digital Microfluidics", accepted for publication in IEEE Transactions on VLSI Systems, 2007, and Artech House, Norwood, MA, 2007.

Paik, "Adaptive Hot-Spot Cooling of Integrated Circuits Using Digital Microfluidics", Dissertation, Dept. of Electrical and Computer Engineering, Duke University, Apr. 25, 2006, 1-188.

Paik et al., "Adaptive hot-spot cooling of integrated circuits using digital microfluidics", Proceedings ASME International Mechanical Engineering Congress and Exposition, Orlando, Florida, USA. IMECE2005-81081, Nov. 5-11, 2005, 1-6.

Paik et al., "Coplanar Digital Microfluidics Using Standard Printed Circuit Board Processes", 9th International Conference on Miniaturized Systems for Chemistry and Life Sciences (MicroTAS), Boston, MA; Poster, 2005.

(56) References Cited

OTHER PUBLICATIONS

Paik et al., "Coplanar Digital Microfluidics Using Standard Printed Circuit Board Processes", 9th Int'l Conf. on Miniaturized Systems for Chemistry and Life Sciences, Boston, MA, Oct. 9-13, 2005, 566-68.

Paik et al., "Droplet-Based Hot Spot Cooling Using Topless Digital Microfluidics on a Printed Circuit Board", Int'l Workshops on Thermal Investigations of ICs and Systems (THERMINIC), 2005, 278-83.

Paik et al., "Electrowetting-based droplet mixers for microfluidic systems", Lab on a Chip (LOC), vol. 3. (more mixing videos available, along with the article, at LOC's website), 2003, 28-33.

Paik et al., "Programmable Flow-Through Real Time PCR Using Digital Microfluidics", Paris, France, Oct. 7-11, 2007, 1559-1561.

Paik et al., "Programmable flow-through real-time PCR using digital microfluidics", Proc. Micro Total Analysis Systems (µTAS), Handout, 2007.

Paik et al., "Programmable flow-through real-time PCR using digital microfluidics", Proc. Micro Total Analysis Systems (µTAS), Poster, 2007.

Paik et al., "Rapid Droplet Mixers for Digital Microfluidic Systems", Masters Thesis, Duke Graduate School., 2002, 1-82.

Paik et al., "Rapid droplet mixers for digital microfluidic systems", Lab on a Chip, vol. 3. (More mixing videos available, along with the article, at LOC's website.), 2003, 253-259.

Paik et al., "Thermal effects on Droplet Transport in Digital Microfluids with Application to Chip Cooling Processing for Integrated Microfluidics", International Conference on Thermal, Mechanics, and Thermomechanical Phenomena in Electronic Systems (ITherm), 2004, 649-654.

Pamula, "A digital microfluidic platform for multiplexed explosive detection", Chapter 18, Electronics Noses and Sensors for the Detection of Explosives, Eds., J.W. Gardner and J. Yinon, Kluwer Academic Publishers, 2004.

Pamula et al., "A droplet-based lab-on-a-chip for colorimetric detection of nitroaromatic explosives", Proceedings of Micro Electro Mechanical Systems, 2005, 722-725.

Pamula et al., "Cooling of integrated circuits using droplet-based microfluidics", Proc. ACM Great Lakes Symposium on VLSI, Apr. 2003, 84-87.

Pamula, "Digital microfluidic lab-on-a-chip for multiplexing tests in newborn screening", Newborn Screening Summit: Envisioning a Future for Newborn Screening, Bethesda, MD, Dec. 7, 2009.

Pamula et al., "Digital microfluidic lab-on-a-chip for protein crystallization", 5th Protein Structure Initiative "Bottlenecks" Workshop, NIH, Bethesda, MD, Apr. 13-14, 2006, I-16.

Pamula et al., "Digital Microfluidic Methods in Diagnosis of Neonatal Biochemical Abnormalities", Developing Safe and Effective Devices and Instruments for Use in the Neonatal Intensive Care for the 21st Century, Pediatric Academic Societies' Annual Meeting, Vancouver, Canada, May 1-4, 2010.

Pamula et al., "Digital Microfluidic Platform for Multiplexing LSD Assays in Newborn Screening", LSD World Meeting, Las Vegas, NV, Feb. 16-18, 2011.

Pamula et al., "Digital Microfluidics Platform for Lab-on-a-chip applications", Duke University Annual Post Doctoral Research Day, 2002.

Pamula et al., "Microfluidic electrowetting-based droplet mixing", IEEE, 2002, 8-10.

Pamula et al., "Rapid LSD assays on a multiplex digital microfluidic platform for newborn screening", Lysosomal Disease Network World Symposium 2012, San Diego, CA, Feb. 8-19, 2012, 39.

Pamula, "Sample Preparation and Processing using Magnetic Beads on a Digital Microfluidic Platform", CHI's Genomic Sample Prep, San Francisco, CA, Jun. 9-10, 2009.

Pamula, "Sample-to-sequence-molecular diagnostics on a digital microfluidic lab on a chip", Pre-conference workshops, 4th International Conference on Birth Defects and Disabilities in the Developing World, New Dehli, India, Oct. 4, 2009.

Panchapakesan, "Droplet Feedback Mechanisms on a Digital Microfluidic Platform and Development of Hyperbilirubinemia Panel", PhD Dissertation, University at Buffalo, State University of New York, Jan. 9, 2013.

Pollack et al., "Applications of Electrowetting-Based Digital Microfluidics in Clinical Diagnostics", Expert Rev. Mol. Diagn., vol. 11(4), 2011, 393-407.

Pollack et al., "Continuous sequencing-by-synthesis-based on a digital microfluidic platform", National Human Genome Research Institute, Advanced DNA Sequencing Technology Development Meeting, Chapel Hill, NC, Mar. 10-11, 2010.

Pollack, et al., "Electrowetting-Based Actuation of Droplets for Integrated Microfluidics", Lab on a Chip (LOC), vol. 2, 2002, 96-101.

Pollack et al., "Electrowetting-based actuation of liquid droplets for microfluidic applications", Appl. Phys. Letters, vol. 77, No. 11, Sep. 11, 2000, 1725-1726.

Pollack, "Electrowetting-based Microactuation of Droplets for Digital Microfluidics", PhD Thesis, Department of Electrical and Computer Engineering, Duke University, 2001.

Pollack et al., "Electrowetting-Based Microfluidics for High-Throughput Screening", smallTalk 2001 Conference Program Abstract, San Diego, Aug. 27-31, 2001, 149.

Pollack et al., "Investigation of electrowetting-based microfluidics for real-time PCR applications", Proc. 7th Int'l Conference on Micro Total Analysis Systems (mTAS), Squaw Valley, CA, Oct. 5-9, 2003, 619-622.

Pollack, "Lab-on-a-chip platform based digital microfluidics", The 6th International Electrowetting Meeting, Aug. 20-22, 2008, 16.

Pollack, "Sample Preparation Using Digital Microfluidics", Sample Prep 2012, Knowledge Press, Inc., May 3-4, 2012.

Punnamaraju, "Voltage and Photo Induced Effects in Droplet-Interface-Bilayer Lipid", PhD Thesis, University of Cincinnati, 2011.

Punnamaraju et al., "Voltage Control of Droplet Interface Bilayer Lipid Membrane Dimensions", Langmuir The ACS Journal of Surfaces and Colloids, vol. 27, Issue 2, 2011, Published on Web, Dec. 10, 2010, 618-626.

Ren et al., "Automated electrowetting-based droplet dispensing with good reproducibility", Proc. Micro Total Analysis Systems (mTAS), 7th Int. Conf.on Miniaturized Chem and Biochem Analysis Systems, Squaw Valley, CA, Oct. 5-9, 2003, 993-996.

Ren et al., "Automated on-chip droplet dispensing with volume control by electro-wetting actuation and capacitance metering", Sensors and Actuators B: Chemical, vol. 98, Mar. 2004, 319-327.

Ren et al., "Design and testing of an interpolating mixing architecture for electrowetting-based droplet-on-chip chemical dilution", Transducers, 12th International Conference on Solid-State Sensors, Actuators and Microsystems, 2003, 619-622.

Ren et al., "Dynamics of electro-wetting droplet transport", Sensors and Actuators B (Chemical), vol. B87, No. 1, Nov. 15, 2002, 201-206.

Ren et al., "Micro/Nano Liter Droplet Formation and Dispensing by Capacitance Metering and Electrowetting Actuation", IEEE-NANO, 2002, 369-372.

Rival et al., "EWOD Digital Microfluidic Device for Single Cells Sample Preparation and Gene Expression Analysis", Lab Automation 2010, Palm Springs Convention Center, Palm Springs, CA, USA; Abstract in Proceedings, Poster distributed at conference, Jan. 23-27, 2010.

Rival et al., "Expression de génes de quelques cellules sur puce EWOD/Gene expression of few cells on EWOD chip", iRTSV,http://www-dsv.cea.fr/var/plain/storage/original/media/File/iRTSV/thema_08(2).pdf (english translation), Winter 2009-2010.

Rival et al., "New insight on droplet dynamics under electrowetting actuation and design tools for speeding up product development", 8th Electrowetting Workshop, Athens, Greece. Abstract, 2012.

Rival et al., "New insight on droplet dynamics under electrowetting actuation and design tools for speeding up product development", 8th Electrowetting Workshop, Athens, Greece, Presentation, 2012.

Rival et al., "Towards Single Cells Gene Expression on EWOD Lab on Chip", ESONN 2008, Grenoble, France; Poster presented, Aug. 26, 2008.

(56) References Cited

OTHER PUBLICATIONS

Rival et al., "Towards single cells gene expression on EWOD lab on chip", ESONN, Grenoble, France, abstract in proceedings, Aug. 2008.
Rival et al., "Towards single cells gene expression preparation and analysis on ewod lab on chip", Nanobio Europe 2009, Poster distributed at conference, Jun. 16-18, 2009.
Rival et al., "Towards single cells gene expression preparation and analysis on ewod lab on chip", Nanobio Europe 2009, Abstract in proceedings, Jun. 16-18, 2009.
Rival et al., "Towards single cells gene expression preparation and analysis on ewod lab on chip", Lab on Chip Europe 2009 poster distributed at Conference, May 19-20, 2009.
Rival et al., "Towards single cells gene expression preparation and analysis on ewod lab on chip", Lab on Chip Europe 2009, Abstract in proceedings, May 19-20, 2009.
Rouse et al., "Digital microfluidics: a novel platform for multiplexing assays used in newborn screening", Poster 47, 41st AACC's Annual Oak Ridge Conference Abstracts, Clinical Chemistry, vol. 55, 2009, 1891.
Sandahl et al., "Automated Multianalyte Screening for Classification of Forensic Samples", 23rd International Symposium for Human Identification, Nashville, TN. http://www.promega.com/~/media/files/resources/conference%20proceedings/ishi%2023/poster%20abstracts/31%20poster.pdf?la=en, Oct. 16-17, 2012.
Schell et al., "Evaluation of a Digital Microfluidic real-time PCR Platform to detect DNA of Candida albicans", Eur. J. Clin Microbiol Infect Dis, Published on-line DOI 10.1007/s10096-012-15616, Feb. 2012.
Sherman et al., "Flow Control by Using High-Aspect-Ratio, In-Plane Microactuators", Sensors and Actuators, vol. 73, 1999, pp. 169-175.
Sherman et al., "In-Plane Microactuator for Fluid Control Application", Proc. IEEE Micro Electro Mechanical Systems Workshop, Heidelberg, Germany, Jan. 1998, pp. 454-459.
Shi et al., "Evaluation of stability of fluorometric reagent kits for screening of Lysosomal Storage Disorders", APHL Newborn Screening and Genetic Testing Symposium, San Diego, 2011.
Sista et al., "96-Immunoassay Digital Microfluidic Multiwell Plate", Proc. µTAS, Oct. 12-16, 2008.
Sista, "Development of a Digital Microfluidic Lab-on-a-Chip for Automated Immunoassays with Magnetically Responsive Beads", PhD Thesis, Department of Chemical Engineering, Florida State University, 2007.
Sista et al., "Development of a digital microfluidic platform for point of care testing", Lab on a chip, vol. 8, Dec. 2008, First published as an Advance Article on the web, Nov. 5, 2008, 2091-2104.
Sista et al., "Development of digital microfluidic assays for galactosemia and biotinidase deficiency in newborn dried blood spot samples", 2013 APHL Newborn Screening and Genetic Testing Symposium and the International Society for Neonatal Screening, Atlanta, GA. Poster presented, abstract in conference proceedings, May 5-10, 2013.
Sista et al., "Development of digital microfluidic assays for galactosemia and biotinidase deficiency in newborn dried blood spot samples", Extended abstract from the 2013 APHL Newborn Screening and Genetic Testing Symposium and the International Society for Neonatal Screening, Atlanta, GA, Extended abstract to be published summer 2013 confirmed.
Sista et al., "Digital Microfluidic Platform for Multiplexing Enzyme Assays: Implications for Lysosomal Storage Disease Screening in Newborns", Clinical Chemistry, vol. 57, Aug. 22, 2011, 1444-51.
Sista et al., "Digital Microfluidic platform for multiplexing LSD assays in newborn screening", APHL Newborn Screening and Genetic Testing Symposium, Orlando, May 3-6, 2010.
Sista et al., "Digital Microfluidic Platform to Consolidate Enzymatic Assays on Dried Blood Spot Samples for Rapid Newborn Screening", 2013 Canadian Newborn and Child Screening Symposium, Ottawa, Canada, Poster, Apr. 11-12, 2013.
Sista et al., "Enzymatic assays on whole blood for lysosomal storage diseases using a digital microfluidic platform", 2013 American Association for Clinical Chemistry (AACC) Annual Meeting, Houston, TX, Abstract accepted for poster presentation, Jul. 28-Aug. 1, 2013.
Sista et al., "Heterogeneous immunoassays using magnetic beads on a digital microfluidic platform", Lab on a Chip, vol. 8, Dec. 2008, First published as an Advance Article on the web, Oct. 14, 2008, 2188-2196.
Sista et al., "Multiplex digital microfluidic platform for newborn screening of lysosomal storage disorders", 2013 Pediatric Academic Societies Annual Meeting PAS (Pediatric Academic Society), Washington, D.C., poster presented, abstract published online http://www.abstracts2view.com/pas/, May 4-7, 2013.
Sista et al., "Multiplex Digital Microfluidic Platform for Rapid Newborn Screening of Lysosomal Storage Disorders", ACMG Annual Meeting, Charlotte, NC, 2012.
Sista et al., "Multiplex Newborn Screening for Pompe, Fabry, Hunter, Gaucher, and Hurler Diseases Using a Digital Microfluidic Platform", Clinica Chimica Acta, vol. 424. available on line http://dx.doi.org/10.1016/j.cca.2013.05.001, May 7, 2013, 12-18.
Sista et al., "Performance of a digital microfluidic assay for Gaucher and Hurler disorders", APHL Newborn Screening and Genetic Testing Symposium, San Diego, 2011.
Sista et al., "Performance of multiple enzymatic assays on dried blood spot samples for rapid newborn screening using digital microfluidics", 2013 Oak Ridge Conference (AACC), Baltimore, MD, poster presentation, Apr. 18-19, 2013.
Sista et al., "Rapid assays for Gaucher and Hurler diseases in dried blood spots using digital microfluidics", Molecular Genetics and Metabolism. vol. 109. Available online http://dx.doi.org/10.1016/j.ymgme.2013.03.010, 2013, 218-220.
Sista et al., "Rapid, Single-Step Assay for Hunter Syndrome in Dried Blood Spots Using Digital Microfluidics", Clinica Chimica Acta, vol. 412, 2011, 1895-97.
Sista et al., "Spatial multiplexing of immunoassays for small-volume samples", 10th PI Meeting IMAT, Bethesda, 2009.
Srinivasan et al., "3-D imaging of moving droplets for microfluidics using optical coherence tomography", Proc. 7th International Conference on Micro Total Analysis Systems (mTAS), Squaw Valley, CA, Oct. 5-9, 2003, 1303-1306.
Srinivasan et al., "A digital microfluidic biosensor for multianalyte detection", Proc. IEEE 16th Annual Int'l Conf. on Micro Electro Mechanical Systems Conference, 2003, 327-330.
Srinivasan, "A Digital Microfluidic Lab-on-a-Chip for Clinical Diagnostic Applications", Ph.D. thesis, Dept of Electrical and Computer Engineering, Duke University, 2005.
Srinivasan et al., "An integrated digital microfluidic lab-on-a-chip for clinical diagnostics on human physiological fluids", Lab on a Chip, vol. 4, 2004, 310-315.
Srinivasan et al., "Clinical diagnostics on human whole blood, plasma, serum, urine, saliva, sweat and tears on a digital microfluidic platform", Proc. 7th International Conference on Micro Total Analysis Systems (mTAS), Squaw Valley, CA, Oct. 5-9, 2003, 1287-1290.
Srinivasan et al., "Commercializing electrowetting-based digital microfluidics: from the lab to a product", 8th International Meeting on Electrowetting, Athens, Greece, Jun. 21-23, 2012.
Srinivasan et al., "Digital Microfluidic Lab-on-a-Chip for Protein Crystallization", The 82nd ACS Colloid and Surface Science Symposium, 2008.
Srinivasan et al., "Digital Microfluidics: a novel platform for multiplexed detection of lysosomal storage diseases for newborn screening", AACC Oak Ridge Conference Abstracts, Clinical Chemistry, vol. 54, 2008, 1934.
Srinivasan et al., "Droplet-based microfluidic lab-on-a-chip for glucose detection", Analytica Chimica Acta, vol. 507, No. 1, 2004, 145-150.
Srinivasan et al., "Electrowetting", Chapter 5, Methods in Bioengineering: Biomicrofabrication and Biomicrofluidics, Ed. J.D. Zahn, ISBN: 9781596934009, Artech House Publishers, 2010.

(56) References Cited

OTHER PUBLICATIONS

Srinivasan et al., "Feasibility of a point of care newborn screening platform for hyperbilirubinemia", APHL Newborn Screening and Genetic Testing Symposium, San Diego, 2011.

Srinivasan et al., "Low cost digital microfluidic platform for protein crystallization", Enabling Technologies for Structural Biology, NIGMS Workshop, Bethesda, MD., Mar. 4-6, 2009, J-23.

Srinivasan et al., "Protein Stamping for MALDI Mass Spectrometry Using an Electrowetting-based Microfluidic Platform", Lab-on-a-Chip: Platforms, Devices, and Applications, Conf. 5591, SPIE Optics East, Philadelphia, Oct. 25-28, 2004.

Srinivasan et al., "Scalable Macromodels for Microelectromechanical Systems", Technical Proc. 2001 Int. Conf. on Modeling and Simulation of Microsystems, 2001, 72-75.

Su et al., "Yield Enhancement of Digital Microfluidics-Based Biochips Using Space Redundancy and Local Reconfiguration", Proc. Design, Automation and Test in Europe (DATE) Conf., IEEE, 2005, 1196-1201.

Sudarsan et al., "Printed circuit technology for fabrication of plastic based microfluidic devices", Analytical Chemistry vol. 76, No. 11, Jun. 1, 2004, Previously published online, May 2004, 3229-3235.

Thwar et al., "DNA sequencing using digital microfluidics", Poster 42, 41st AACC's Annual Oak Ridge Conference Abstracts, Clinical Chemistry vol. 55, 2009, 1891.

Tolun et al., "A Novel Fluorometric Enzyme Analysis Method for Hunter Syndrome Using Dried Blood Spots", Mol. Genet. Metab., 105, Issue 3, 2012; doi:10.1016/j.ymgme.2011.12.011, Epub, Dec. 21, 2011, 519-521.

Tolun et al., "Dried blood spot based enzyme assays for lysosomal storage disorders", 2011 Tokyo Meeting on Lysosomal Storage Disease Screening, Tokyo, Aug. 5, 2011.

Wang et al., "Comparison of enzyme activities for Pompe, Fabry, and Gaucher diseases on CDC's Quality Control spots between microplate fluorometry, mass spectrometry, and digital microfluidic fluorometry", APHL Newborn Screening and Genetic Testing Symposium, San Diego, 2011.

Wang et al., "Droplet-based micro oscillating-flow PCR chip", J. Micromechanics and Microengineering, vol. 15, 2005, 1369-1377.

Wang et al., "Efficient in-droplet separation of magnetic particles for digital microfluidics", Journal of Micromechanics and Microengineering, vol. 17, 2007, 2148-2156.

Weaver, "Application of Magnetic Microspheres for Pyrosequencing on a Digital Microfluidic Platform", Department of Electrical and Computer Engineering, Duke University, 2005.

Wulff-Burchfield et al., "Microfluidic platform versus conventional real-time polymerase chain reaction for the detection of Mycoplasma pneumoniae in respiratory specimens", Diagnostic Microbiology and Infectious Disease, vol. 67, 2010, 22-29.

Xu et al., "A Cross-Referencing-Based Droplet Manipulation Method for High-Throughput and Pin-Constrained Digital Microfluidic Arrays", Proceedings of conference on Design, Automation and Test in Europe, Apr. 2007.

Xu et al., "Automated Design of Pin-Constrained Digital Microfluidic Biochips Under Droplet-Interference Constraints", ACM Journal on Emerging Technologies is Computing Systems, vol. 3(3), 2007, 14:1-14:23.

Xu et al., "Automated solution preparation on a digital microfluidic lab-on-chip", PSI Bottlenecks Workshop, 2008.

Xu et al., "Automated, Accurate and Inexpensive Solution-Preparation on a Digital Microfluidic Biochip", Proc. IEEE Biomedical Circuits and Systems Conference (BioCAS), 2008, 301-304.

Xu et al., "Defect-Aware Synthesis of Droplet-Based Microfluidic Biochips", IEEE, 20th International Conference on VLSI Design, 2007.

Xu et al., "Defect-Tolerant Design and Optimization of a Digital Microfluidic Biochip for Protein Crystallization", IEEE Transactions on Computer Aided Design, vol. 29, No. 4, 2010, 552-565.

Xu et al., "Design and Optimization of a Digital Microfluidic Biochip for Protein Crystallization", Proc. IEEE/ACM International Conference on Computer-Aided Design (ICCAD), Nov. 2008, 297-301.

Xu et al., "Digital Microfluidic Biochip Design for Protein Crystallization", IEEE-NIH Life Science Systems and Applications Workshop, LISA, Bethesda, MD, Nov. 8-9, 2007, 140-143.

Xu et al., "Droplet-Trace-Based Array Partitioning and a Pin Assignment Algorithm for the Automated Design of Digital Microfluidic Biochips", CODES, 2006, 112-117.

Xu et al., "Integrated Droplet Routing in the Synthesis of Microfluidic Biochips", IEEE, 2007, 948-953.

Xu et al., "Parallel Scan-Like Test and Multiple-Defect Diagnosis for Digital Microfluidic Biochips", IEEE Transactions on Biomedical Circuits and Systems, vol. 1(2), Jun. 2007, 148-158.

Xu et al., "Parallel Scan-Like Testing and Fault Diagnosis Techniques for Digital Microfluidic Biochips", Proceedings of the 12th IEEE European Test Symposium (ETS), Freiburg, Germany, May 20-24, 2007, 63-68.

Yang et al., "Manipulation of droplets in microfluidic systems", Trends in Analytical Chemistry, vol. 29, Feb. 2010, 141-157.

Yao et al., "Spot Cooling Using Thermoelectric Microcooler", Proc. 18th Int. Thermoelectric Conf, Baltimore, VA, pp. 256-259, Aug. 1999.

Yi et al., "Channel-to-droplet extractions for on-chip sample preparation", Solid-State Sensor, Actuators and Microsystems Workshop (Hilton Head '06), Hilton Head Island, SC, Jun. 2006, 128-131.

Yi et al., "Characterization of electrowetting actuation on addressable single-side coplanar electrodes", Journal of Micromechanics and Microengineering, vol. 16.,Oct. 2006, 2053-2059.

Yi et al., "EWOD Actuation with Electrode-Free Cover Plate", Digest of Tech. papers,13th International Conference on Solid-State Sensors, Actuators and Microsystems (Transducers '05), Seoul, Korea, Jun. 5-9, 2005, 89-92.

Yi et al., "Geometric surface modification of nozzles for complete transfer of liquid drops", Solid-State Sensor, Actuator and Microsystems Workshop, Hilton Head Island, South Carolina, Jun. 6-10, 2004, 164-167.

Yi, "Soft Printing of Biological Liquids for Micro-arrays: Concept, Principle, Fabrication, and Demonstration", Ph.D. dissertation, UCLA, 2004.

Yi et al., "Soft Printing of Droplets Digitized by Electrowetting", Transducers 12th Int'l Conf. on Solid State Sensors, Actuators and Microsystems, Boston, Jun. 8-12, 2003, 1804-1807.

Yi et al., "Soft Printing of Droplets Pre-Metered by Electrowetting", Sensors and Actuators A: Physical, vol. 114, Jan. 2004, 347-354.

Zeng et al., "Actuation and Control of Droplets by Using Electrowetting-on-Dielectric", Chin. Phys. Lett., vol. 21(9), 2004, 1851-1854.

Zhao et al., "Droplet Manipulation and Microparticle Sampling on Perforated Microfilter Membranes", J. Micromech. Microeng., vol. 18, 2008, 1-11.

Zhao et al., "In-droplet particle separation by travelling wave dielectrophoresis (twDEP) and EWOD", Solid-State Sensor, Actuators and Microsystems Workshop (Hilton Head '06), Hilton Head Island, SC, Jun. 2006, 181-184.

Zhao et al., "Micro air bubble manipulation by electrowetting on dielectric (EWOD): transporting, splitting, merging and eliminating of bubbles", Lab on a chip, vol. 7, 2007, First published as an Advance Article on the web, Dec. 4, 2006, 273-280.

Zhao et al., "Microparticle Concentration and Separation byTraveling-Wave Dielectrophoresis (twDEP) for Digital Microfluidics", J. Microelectromechanical Systems, vol. 16, No. 6, Dec. 2007, 1472-1481.

Zhao et al., "Optimization Techniques for the Synchronization of Concurrent Fluidic Operations in Pin-Constrained Digital Microfluidic Biochips", IEEE Transactions on Very Large Scale Integration (VLSI) Systems, vol. 20, No. 6, Jun. 2012, 1132-1145.

Zhao et al., "Synchronization of Concurrently-Implemented Fluidic Operations in Pin-Constrained Digital Microfluidic Biochips", VLSI Design, (Best Paper Award), 2010.

(56) References Cited

OTHER PUBLICATIONS

International Preliminary Report on Patentability dated Apr. 21, 2015 from PCT International Application No. PCT/US2013/064797.
International Search Report dated Jan. 24, 2014 for corresponding PCT International Application No. PCT/US2013/064797.

* cited by examiner

DIGITAL MICROFLUIDICS CARTRIDGE AND SYSTEM FOR OPERATING A FLOW CELL

1 RELATED APPLICATIONS

In addition to the patent applications cited herein, each of which is incorporated herein by reference, this patent application is a 371 National Entry of International PCT Application No.: PCT/US2013/064797, with an international filing date of Oct. 14, 2013, entitled "Digital Microfluidics Cartridge and System for Operating a Flow Cell", the application of which is related to and claims priority to U.S. Provisional Patent Application No. 61/714,002, filed on Oct. 15, 2012, entitled "Flow Cells"; U.S. Provisional Patent Application No. 61/714,484, filed on Oct. 16, 2012, entitled "Flow Cells"; and U.S. Provisional Patent Application No. 61/723,596, filed on Nov. 7, 2012 entitled "Digital Microfluidics (DMF)-Based Liquid Handling System (LHS) for Supplying Liquids to a Flow Cell (FC)", the entire disclosures of which are incorporated herein by reference.

2 FIELD OF THE PRESENT DISCLOSURE

The present disclosure relates to a droplet actuator that is used to supply liquids to a flow cell.

3 BACKGROUND

A droplet actuator typically includes one or more substrates configured to form a surface or gap for conducting droplet operations. The one or more substrates establish a droplet operations surface or gap for conducting droplet operations and may also include electrodes arranged to conduct the droplet operations. The droplet operations substrate or the gap between the substrates may be coated or filled with a filler liquid that is immiscible with the liquid that forms the droplets.

Sequencing-by-synthesis (SBS) is a DNA sequencing strategy in which a template strand of DNA is used to synthesize its complement. Typically, SBS operates in a cyclical fashion wherein one or more nucleotide bases are added to a reaction containing the DNA templates, DNA polymerase, and other factors necessary to incorporate the next complementary bases into the synthesized strand. Depending on the specifics of the technology, a signal is then produced which enables one to infer the identity of the complementary bases incorporated into the synthesized strand. Although some approaches use a free-running enzyme to continuously synthesize a new strand, the majority of approaches currently in use require that the incorporation reactions remain synchronized at each cycle. This is typically achieved by either offering only one of the four nucleotide bases at a time or by using nucleotide bases that have reversible chemical blocks that prevent more than one base from being incorporated in any given cycle. Simple washing or reaction with de-blocking reagents is used between each cycle to prepare the DNA templates for the subsequent incorporation step. A single SBS experiment may incorporate 100s of these cycles leading to a need for very rapid and efficient liquid handling to cycle through the various liquid reagents used in each step.

Next-generation sequencing (NGS) systems employing SBS typically use flow-cells (FC) in which millions of these reactions are performed in parallel on a glass or silicon surface or upon the surfaces of microscopic beads. The FC serves to confine the reactions within a defined area where the signals can be conveniently detected, typically either by optical or electrical means. The liquid reagents are typically contained in tubes, plates, cartridges, or other disposable receptacles. A liquid-handling system (LHS) consisting of tubes, pumps, and valves is typically situated between the liquid reagents and the FC. The LHS conveys the liquids through the FC in a predetermined sequence dictated by the specific chemistry and the physical properties of the FC and LHS. Typically, the LHS utilizes valves to switch between the different liquid sources. These valves may be located some distance away from the FC. Thus a dead volume exists between each liquid source and the FC. This dead volume limits the efficiency of reagent utilization as well as the time required to switch between liquids. Therefore, there is a need for more efficient methods of liquid switching that are both more efficient in terms of reagent consumption and faster in terms of their ability to completely replace one liquid in the FC with a second liquid as the various steps in an NGS SBS protocol are performed.

Additionally, liquid-handling systems currently rely on the use of mechanical pumps and valves. Mechanisms with moving parts, such as these pumps and valves, are frequently found to be unreliable and difficult to maintain and operate. Therefore, there is a need for more simple liquid-handling systems that are less expensive, more reliable, and easier to operate.

4 BRIEF DESCRIPTION OF THE PRESENT DISCLOSURE

In one embodiment, the present disclosure provides a digital microfluidic liquid handling system for supplying liquids to a flow cell. The digital microfluidic liquid handling system may include a droplet actuator, wherein the droplet actuator may include a bottom substrate separated from a top substrate to form a droplet operations gap, wherein the droplet operations gap is filled with a filler fluid; liquid reservoirs; an electrode arrangement disposed on the bottom and/or top substrate comprising at least one of a path, line, loop, and array of droplet operations electrodes; and a flow cell fluidly coupled to the droplet operations gap through an opening in one of the bottom substrate, the top substrate, or a side-wall. The flow cell may be an external flow cell. The one or more of the liquid reservoirs may be external reservoirs fluidly coupled to the droplet operations gap through a second opening in one of the bottom substrate or top substrate. The one or more external reservoirs may include a gravity-driven liquid dispenser. The electrode arrangement may be configured for supplying liquids to the flow cell in a predetermined sequence. The electrode arrangement may include one or more of reservoir electrodes, droplet operations electrodes, outlet electrodes, and waste well electrodes. The reservoir electrodes may correspond to one of the liquid reservoirs. The electrode arrangement may include electrowetting electrodes. The outlet electrodes may be arranged proximal to the opening. At least a portion of the electrode arrangement may be configured as a loop and a portion may be configured as a snaking path. The snaking path may be configured to provide a cache for accumulating and storing droplets between their source and destination. The electrode arrangement may be disposed on the bottom substrate. The electrode arrangement may be disposed on a side of the bottom substrate that is facing the droplet operations gap. The conductive layer may be disposed on the top substrate. The conductive layer may be disposed on a side of the top substrate that is facing the droplet operations gap. The conductive layer may be configured as a ground reference plane with respect to the electrode arrangement. The height of the droplet operations gap may vary. The height of the droplet operations gap at a reservoir electrode may be greater than a height of the droplet operations gap at the droplet operation electrodes. The opening may be substantially aligned with the outlet electrodes. The opening may be fluidly coupled to an inlet of the flow cell via a tube. The system may further include a pump configured for providing negative pressure on the end of the tube at the flow cell and causing liquid to flow from the opening through the tube and then through the flow cell. The one or more of the liquid reservoirs may share a common electrode pathway. The one or more of the liquid reservoirs may have a dedicated electrode pathway. The dedicated pathway may be from the liquid reservoir to the outlet electrodes. The waste well electrodes may be proximal to the outlet electrodes. The electrode arrangement may include a substantially radial architecture with respect to the outlet electrodes. The gravity-driven liquid dispenser may include a vessel; an outlet; and an inlet at a defined height from the outlet. The inlet may include a hydrophobic pore. The gravity-driven liquid dispenser may be associated with a reservoir electrode of the electrode arrangement. The outlet may be fluidly coupled to the droplet operations gap and aligned with the reservoir electrode. The flow cell may be integrated into the droplet actuator. The electrode arrangement may include one or more electrodes whose surfaces may include one or more hydrophilic spots.

In another embodiment, the present disclosure provides a method of supplying liquids to a flow cell using a digital microfluidic liquid handling system. The method may include, dispensing one or more droplets from one or more liquid reservoirs onto an electrode arrangement of a droplet actuator, the electrode arrangement comprising droplet operations electrodes; transferring the one or more droplets between one or more reservoir electrodes using droplet operations; and transferring the one or more droplets to a flow cell in a predetermined sequence. The method may further include transferring the one or more droplets to a second electrode arrangement after transferring the one or more droplets between one or more reservoir electrodes using droplet operations. The electrode arrangement for transferring the one or more droplets between the one or more reservoirs may include a loop configuration. The second electrode arrangement may include a snaking path configuration. The electrode arrangement may include a radial architecture, wherein each of the one or more reservoir electrodes may have its own dedicated arrangement of droplet operations electrodes leading to the flow cell. The one or more droplets may be transferred to the flow cell in a predetermined sequence for performing sequencing chemistry, such as sequencing-by-synthesis.

In yet another embodiment, the present disclosure provides a digital microfluidic liquid handling system for supplying liquids to a flow cell. The system may include a processor for executing code and a memory in communication with the processor, the system may include code stored in the memory that causes the processor at least to: dispense one or more droplets from one or more liquid reservoirs onto an electrode arrangement in a droplet operations gap of a droplet actuator, the electrode arrangement may include droplet operations electrodes, and wherein the droplet actuator further may include a top substrate and a bottom substrate separated to form the droplet operations gap; fill the droplet operations gap of the droplet actuator with a filler fluid; transfer the one or more droplets between one or more reservoir electrodes of the droplet actuator using droplet operations; and transfer the one or more droplets to a flow cell in a predetermined sequence.

In still yet another embodiment, the present disclosure provides a computer readable medium storing processor executable instructions for performing a method of supplying liquids to a flow cell using a digital microfluidic liquid handling system. The method may include providing a droplet actuator, including a bottom substrate separated from a top substrate to form a droplet operations gap, wherein the droplet operations gap may be filled with a filler fluid; liquid reservoirs; an electrode arrangement disposed on the bottom and/or top substrate including at least one of a path, line, loop, and array of droplet operations electrodes; filling the droplet operations gap of the droplet actuator with a filler fluid; dispensing one or more droplets from one or more of the liquid reservoirs onto the electrode arrangement of the droplet actuator; transferring the one or more droplets between one or more reservoir electrodes of the droplet actuator using droplet operations; and transferring the one or more droplets to a flow cell in a predetermined sequence.

These and other embodiments are described more fully below.

5 BRIEF DESCRIPTION OF THE DRAWINGS

Figure 1:
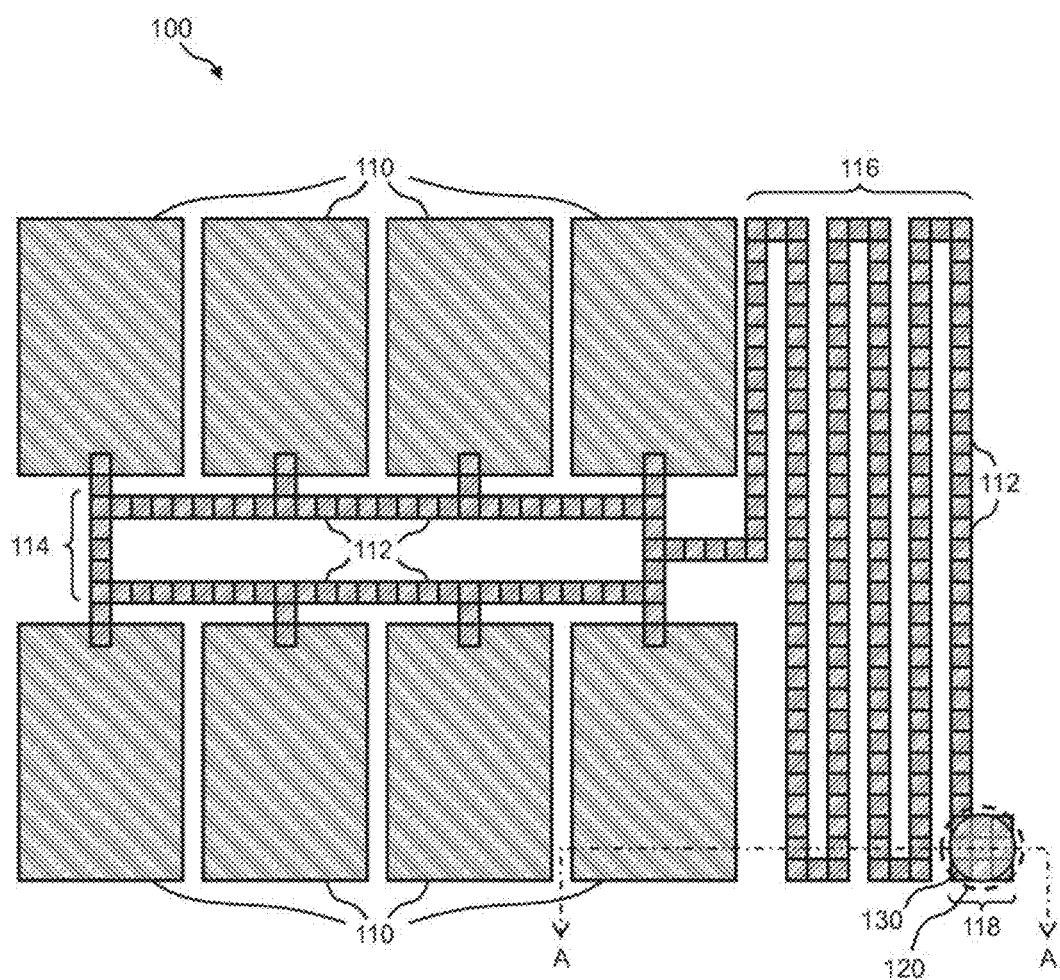
FIG. 1 illustrates a top view of an example of an electrode arrangement of a LHS for supplying liquids to a flow cell.
Figure 5:
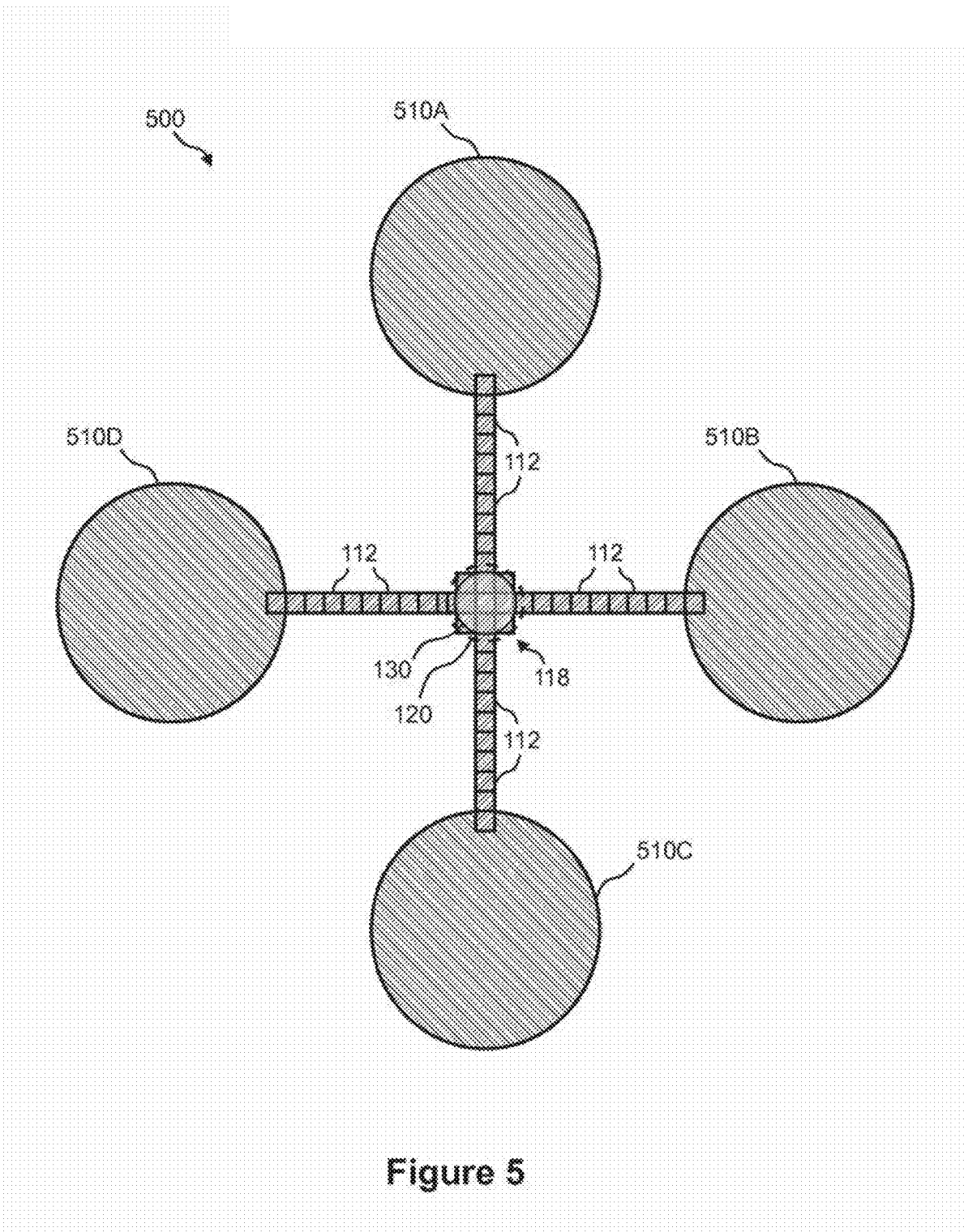
FIG. 5 illustrates a top view of still another example of an electrode arrangement of a LHS for supplying liquids to a flow cell.
Figure 10:
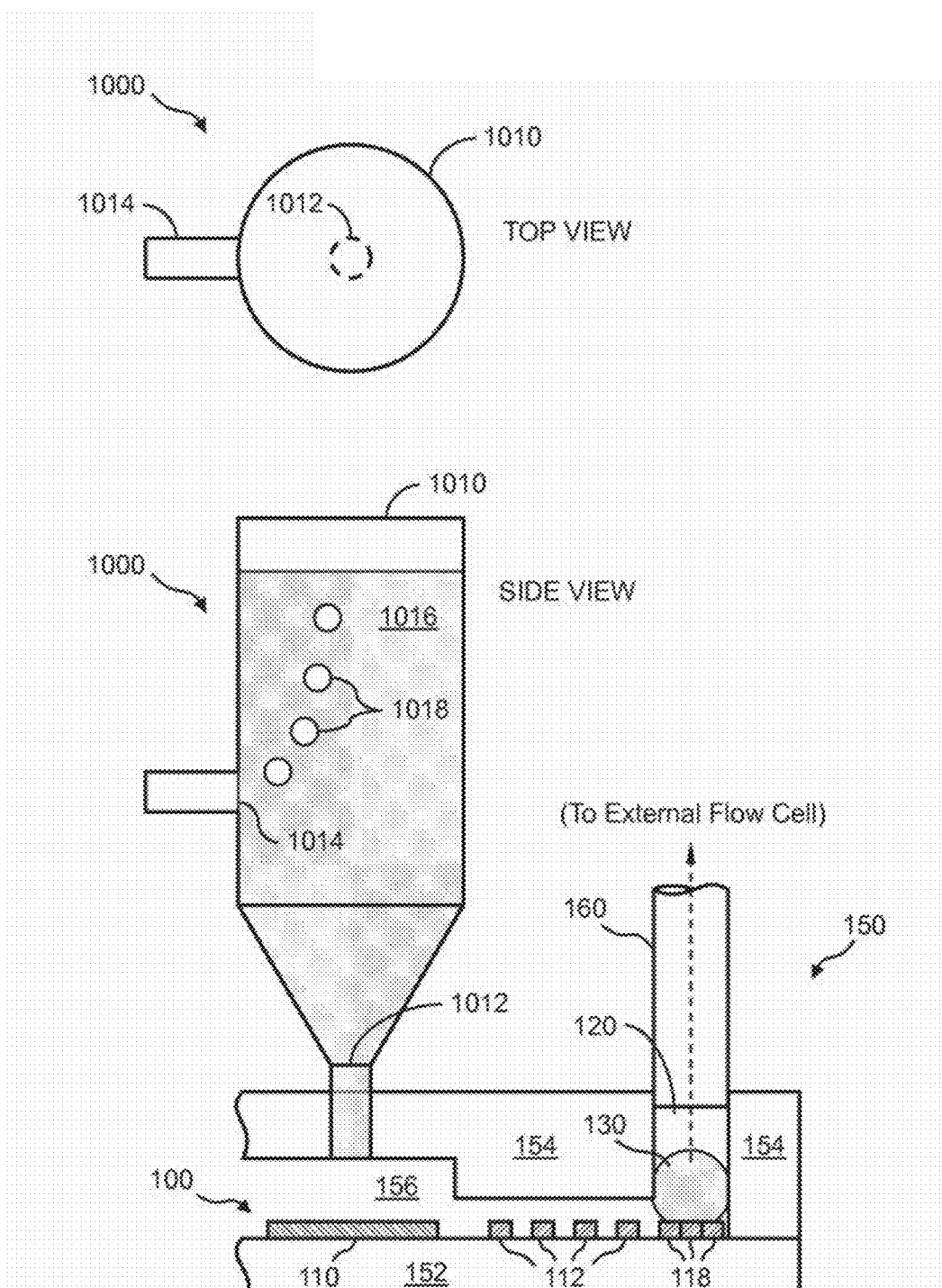
Figure 11A:
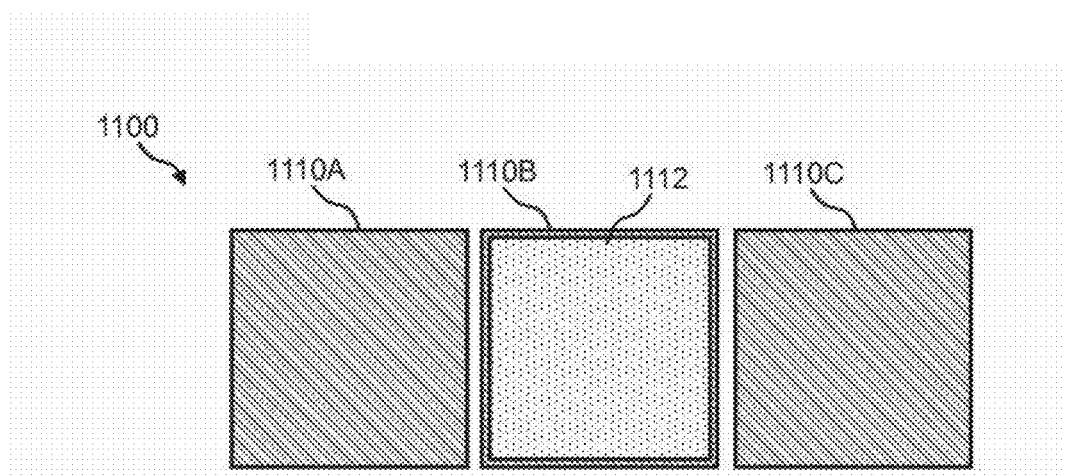
Figure 11B:
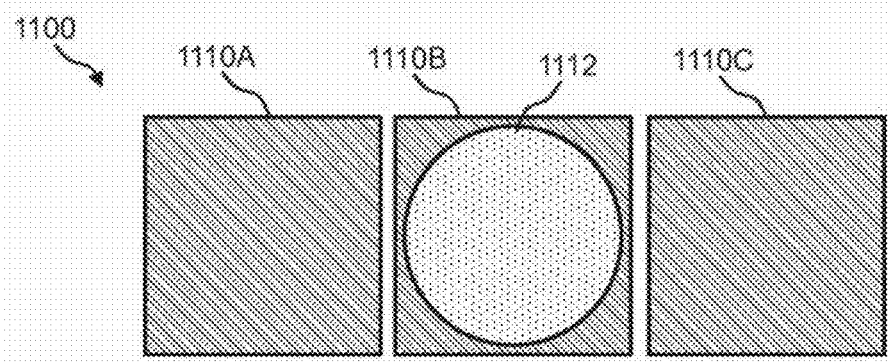
Figure 11C:
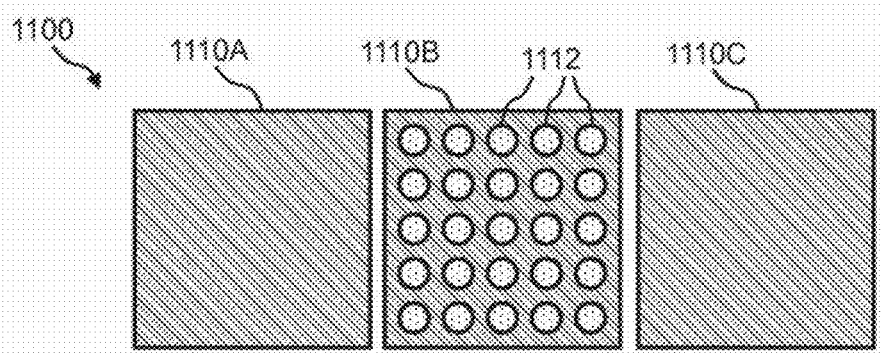
Figure 12:
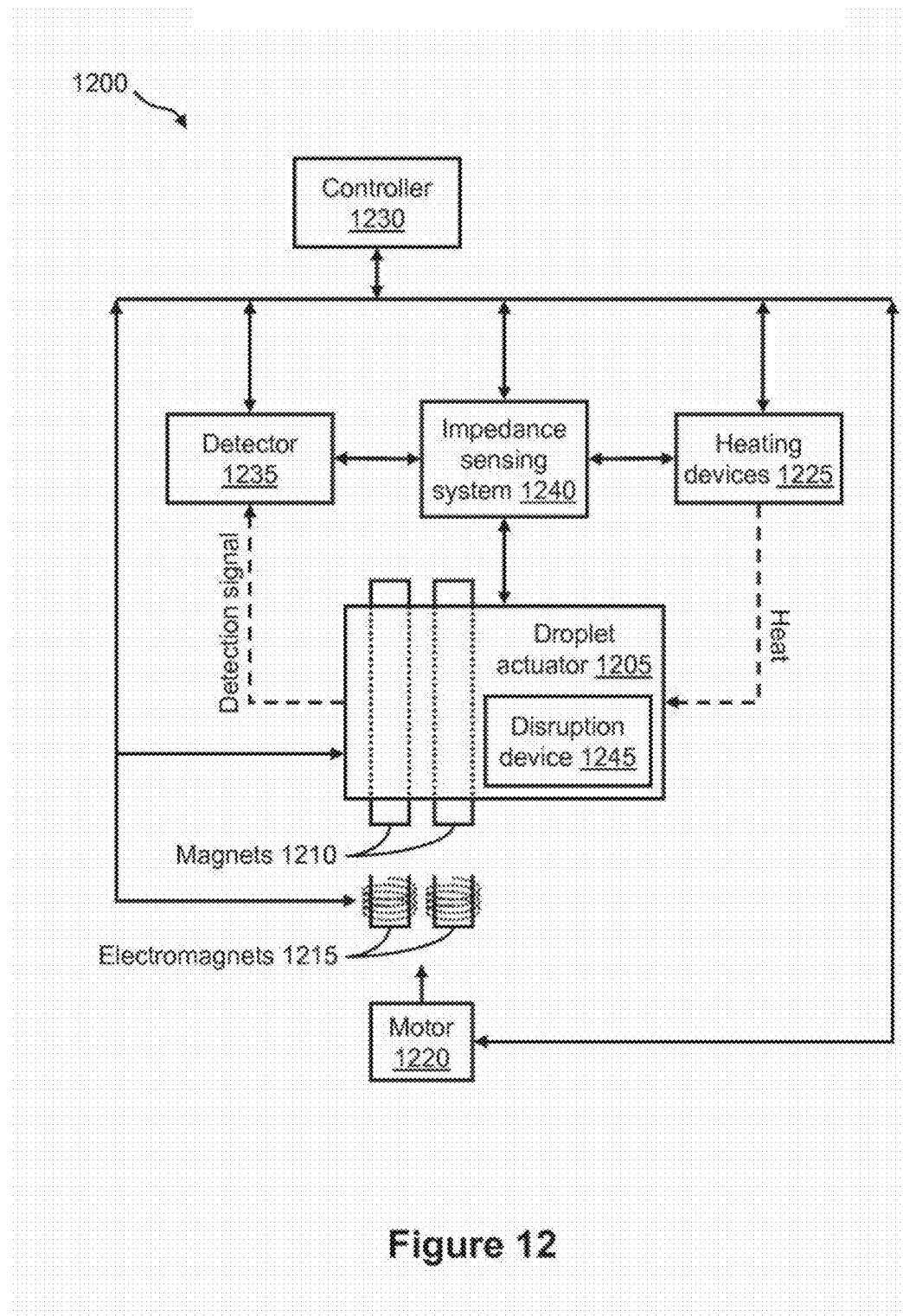

FIGS. 6, 7, 8, and 9 illustrate top views of the electrode arrangement of FIG. 5 and a process of transporting liquid to an outlet port;

FIG. 10 illustrates another cross-sectional view of a portion of the electrode arrangement of FIG. 1, showing a gravity-driven constant pressure head dispenser for delivering a large volume of liquid to the LHS;

FIGS. 11A, 11B, and 11C illustrate top views of examples of electrode arrangements for performing SBS reactions within the droplet actuator rather than in an external flow cell; and FIG. 12 illustrates a functional block diagram of an example of a microfluidics system that includes a droplet actuator.

6 DEFINITIONS

As used herein, the following terms have the meanings indicated.

"Activate," with reference to one or more electrodes, means affecting a change in the electrical state of the one or more electrodes which, in the presence of a droplet, results in a droplet operation. Activation of an electrode can be accomplished using alternating or direct current. Any suitable voltage may be used. For example, an electrode may be activated using a voltage which is greater than about 150 V, or greater than about 200 V, or greater than about 250 V, or from about 275 V to about 1000 V, or about 300 V. Where alternating current is used, any suitable frequency may be employed. For example, an electrode may be activated using alternating current having a frequency from about 1 Hz to about 10 MHz, or from about 10 Hz to about 60 Hz, or from about 20 Hz to about 40 Hz, or about 30 Hz.

"Bubble" means a gaseous bubble in the filler fluid of a droplet actuator. In some cases, bubbles may be intentionally included in a droplet actuator, such as those described in U.S. Patent Pub. No. 20100190263, entitled "Bubble Techniques for a Droplet Actuator," published on Jul. 29, 2010, the entire disclosure of which is incorporated herein by references. The present disclosure relates to undesirable bubbles which are formed as a side effect of various processes within a droplet actuator, such as evaporation or hydrolysis of a droplet in a droplet actuator. A bubble may be at least partially bounded by filler fluid. For example, a bubble may be completely surrounded by filler fluid or may be bounded by filler fluid and one or more surfaces of the droplet actuator. As another example, a bubble may be bounded by filler fluid, one or more surfaces of the droplet actuator, and/or one or more droplets in the droplet actuator.

"Droplet" means a volume of liquid on a droplet actuator that is at least partially bounded by a filler fluid. Droplets may, for example, be aqueous or non-aqueous or may be mixtures or emulsions including aqueous and non-aqueous components. Droplets may take a wide variety of shapes; nonlimiting examples include generally disc shaped, slug shaped, truncated sphere, ellipsoid, spherical, partially compressed sphere, hemispherical, ovoid, cylindrical, combinations of such shapes, and various shapes formed during droplet operations, such as merging or splitting or formed as a result of contact of such shapes with one or more surfaces of a droplet actuator. For examples of droplet fluids that may be subjected to droplet operations using the approach of the present disclosure, see International Patent Application No. PCT/US 06/47486, entitled, "Droplet-Based Biochemistry," filed on Dec. 11, 2006. In various embodiments, a droplet may include a biological sample, such as whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, liquids containing single or multiple cells, liquids containing organelles, fluidized tissues, fluidized organisms, liquids containing multi-celled organisms, biological swabs and biological washes. Moreover, a droplet may include a reagent, such as water, deionized water, saline solutions, acidic solutions, basic solutions, detergent solutions and/or buffers. A droplet can include nucleic acids, such as DNA, genomic DNA, RNA, mRNA or analogs thereof; nucleotides such as deoxyribonucleotides, ribonucleotides or analogs thereof such as analogs having terminator moieties such as those described in Bentley et al., *Nature* 456:53-59 (2008), WO 04/018497; U.S. Pat. No. 7,057,026; WO 91/06678; WO 07/123744; U.S. Pat. No. 7,329,492; U.S. Pat. No. 7,211,414; U.S. Pat. No. 7,315,019; U.S. Pat. No. 7,405,281, and US 2008/0108082, each of which is incorporated herein by reference; enzymes such as polymerases, ligases, recombinases, or transposases; binding partners such as antibodies, epitopes, streptavidin, avidin, biotin, lectins or carbohydrates; or other biochemically active molecules. Other examples of droplet contents include reagents, such as a reagent for a biochemical protocol, such as a nucleic acid amplification protocol, an affinity-based assay protocol, an enzymatic assay protocol, a sequencing protocol, and/or a protocol for analyses of biological fluids. A droplet may include one or more beads.

"Droplet Actuator" means a device for manipulating droplets. For examples of droplet actuators, see Pamula et al., U.S. Pat. No. 6,911,132, entitled "Apparatus for Manipulating Droplets by Electrowetting-Based Techniques," issued on Jun. 28, 2005; Pamula et al., U.S. patent application Ser. No. 11/343,284, entitled "Apparatuses and Methods for Manipulating Droplets on a Printed Circuit Board," filed on filed on Jan. 30, 2006; Pollack et al., International Patent Application No. PCT/US2006/047486, entitled "Droplet-Based Biochemistry," filed on Dec. 11, 2006; Shenderov, U.S. Pat. No. 6,773,566, entitled "Electrostatic Actuators for Microfluidics and Methods for Using Same," issued on Aug. 10, 2004 and U.S. Pat. No. 6,565,727, entitled "Actuators for Microfluidics Without Moving Parts," issued on Jan. 24, 2000; Kim and/or Shah et al., U.S. patent application Ser. No. 10/343,261, entitled "Electrowetting-driven Micropumping," filed on Jan. 27, 2003, Ser. No. 11/275,668, entitled "Method and Apparatus for Promoting the Complete Transfer of Liquid Drops from a Nozzle," filed on Jan. 23, 2006, Ser. No. 11/460,188, entitled "Small Object Moving on Printed Circuit Board," filed on Jan. 23, 2006, Ser. No. 12/465,935, entitled "Method for Using Magnetic Particles in Droplet Microfluidics," filed on May 14, 2009, and Ser. No. 12/513,157, entitled "Method and Apparatus for Real-time Feedback Control of Electrical Manipulation of Droplets on Chip," filed on Apr. 30, 2009; Velev, U.S. Pat. No. 7,547,380, entitled "Droplet Transportation Devices and Methods Having a Fluid Surface," issued on Jun. 16, 2009; Sterling et al., U.S. Pat. No. 7,163,612, entitled "Method, Apparatus and Article for Microfluidic Control via Electrowetting, for Chemical, Biochemical and Biological Assays and the Like," issued on Jan. 16, 2007; Becker and Gascoyne et al., U.S. Pat. No. 7,641,779, entitled "Method and Apparatus for Programmable fluidic Processing," issued on Jan. 5, 2010, and U.S. Pat. No. 6,977,033, entitled "Method and Apparatus for Programmable fluidic Processing," issued on Dec. 20, 2005; Decre et al., U.S. Pat. No. 7,328,979, entitled "System for Manipulation of a Body of Fluid," issued on Feb. 12, 2008; Yamakawa et al., U.S. Patent Pub. No. 20060039823, entitled "Chemical Analysis Apparatus," published on Feb. 23, 2006; Wu, International Patent Pub. No. WO/2009/003184, entitled "Digital Microfluidics Based Apparatus for Heat-exchanging Chemical Processes," published on Dec. 31, 2008; Fouillet et al., U.S. Patent Pub. No. 20090192044, entitled "Electrode Addressing Method," published on Jul. 30, 2009; Fouillet et al., U.S. Pat. No. 7,052,244, entitled "Device for Displacement of Small Liquid Volumes Along a Micro-catenary Line by Electrostatic Forces," issued on May 30, 2006; Marchand et al., U.S. Patent Pub. No. 20080124252, entitled "Droplet Microreactor," published on May 29, 2008; Adachi et al., U.S. Patent Pub. No. 20090321262, entitled "Liquid Transfer Device," published on Dec. 31, 2009; Roux et al., U.S. Patent Pub. No. 20050179746, entitled "Device for Controlling the Displacement of a Drop Between two or Several Solid Substrates," published on Aug. 18, 2005; Dhindsa et al., "Virtual Electrowetting Channels: Electronic Liquid Transport with Continuous Channel Functionality," Lab Chip, 10:832-836 (2010); the entire disclosures of which are incorporated herein by reference, along with their priority documents. Certain droplet actuators will include one or more substrates arranged with a droplet operations gap between them and electrodes associated with (e.g., layered on, attached to, and/or embedded in) the one or more substrates and arranged to conduct one or more droplet operations. For example, certain droplet actuators will include a base (or bottom) substrate, droplet operations electrodes associated with the substrate, one or more dielectric layers atop the substrate and/or electrodes, and optionally one or more hydrophobic layers atop the substrate, the dielectric layers and/or the electrodes forming a droplet operations surface. A top substrate may also be provided, which is separated from the droplet operations surface by a gap, commonly referred to as a droplet operations gap. Various electrode arrangements on the top and/or bottom substrates are discussed in the above-referenced patents and applications and certain novel electrode arrangements are discussed in the description of the present disclosure. During droplet operations it is preferred that droplets remain in continuous contact or frequent contact with a ground or reference electrode. A ground or reference electrode may be associated with the top substrate facing the gap, the bottom substrate facing the gap, and/or in the gap. Where electrodes are provided on both substrates, electrical contacts for coupling the electrodes to a droplet actuator instrument for controlling or monitoring the electrodes may be associated with one or both plates. In some cases, electrodes on one substrate are electrically coupled to the other substrate so that only one substrate is in contact with the droplet actuator. In one embodiment, a conductive material (e.g., an epoxy, such as MASTER BOND™ Polymer System EP79, available from Master Bond, Inc., Hackensack, N.J.) provides the electrical connection between electrodes on one substrate and electrical paths on the other substrates, e.g., a ground electrode on a top substrate may be coupled to an electrical path on a bottom substrate by such a conductive material. Where multiple substrates are used, a spacer may be provided between the substrates to determine the height of the gap therebetween and define dispensing reservoirs. The spacer height may, for example, be at least about 5 μm, 100 μm, 200 μm, 250 μm, 275 μm or more. Alternatively or additionally the spacer height may be at most about 600 μm, 400 μm, 350 μm, 300 μm, or less. The spacer may, for example, be formed of a layer of projections form the top or bottom substrates, and/or a material inserted between the top and bottom substrates. One or more openings may be provided in the one or more substrates for forming a fluid path through which liquid may be delivered into the droplet operations gap. The one or more openings may in some cases be aligned for interaction with one or more electrodes, e.g., aligned such that liquid flowed through the opening will come into sufficient proximity with one or more droplet operations electrodes to permit a droplet operation to be effected by the droplet operations electrodes using the liquid. The base (or bottom) and top substrates may in some cases be formed as one integral component. One or more reference electrodes may be provided on the base (or bottom) and/or top substrates and/or in the gap. Examples of reference electrode arrangements are provided in the above referenced patents and patent applications. In various embodiments, the manipulation of droplets by a droplet actuator may be electrode mediated, e.g., electrowetting mediated or dielectrophoresis mediated or Coulombic force mediated. Examples of other techniques for controlling droplet operations that may be used in the droplet actuators of the present disclosure include using devices that induce hydrodynamic fluidic pressure, such as those that operate on the basis of mechanical principles (e.g. external syringe pumps, pneumatic membrane pumps, vibrating membrane pumps, vacuum devices, centrifugal forces, piezoelectric/ultrasonic pumps and acoustic forces); electrical or magnetic principles (e.g. electroosmotic flow, electrokinetic pumps, ferrofluidic plugs, electrohydrodynamic pumps, attraction or repulsion using magnetic forces and magnetohydrodynamic pumps); thermodynamic principles (e.g. bubble generation/phase-change-induced volume expansion); other kinds of surface-wetting principles (e.g. electrowetting, and optoelectrowetting, as well as chemically, thermally, structurally and radioactively induced surface-tension gradients); gravity; surface tension (e.g., capillary action); electrostatic forces (e.g., electroosmotic flow); centrifugal flow (substrate disposed on a compact disc and rotated); magnetic forces (e.g., oscillating ions causes flow); magnetohydrodynamic forces; and vacuum or pressure differential. In certain embodiments, combinations of two or more of the foregoing techniques may be employed to conduct a droplet operation in a droplet actuator of the present disclosure. Similarly, one or more of the foregoing may be used to deliver liquid into a droplet operations gap, e.g., from a reservoir in another device or from an external reservoir of the droplet actuator (e.g., a reservoir associated with a droplet actuator substrate and a flow path from the reservoir into the droplet operations gap). Droplet operations surfaces of certain droplet actuators of the present disclosure may be made from hydrophobic materials or may be coated or treated to make them hydrophobic. For example, in some cases some portion or all of the droplet operations surfaces may be derivatized with low surface-energy materials or chemistries, e.g., by deposition or using in situ synthesis using compounds such as poly- or per-fluorinated compounds in solution or polymerizable monomers. Examples include TEFLON® AF (available from DuPont, Wilmington, Del.), members of the cytop family of materials, coatings in the FLUOROPEL® family of hydrophobic and superhydrophobic coatings (available from Cytonix Corporation, Beltsville, Md.), silane coatings, fluorosilane coatings, hydrophobic phosphonate derivatives (e.g., those sold by Aculon, Inc), and NOVEC™ electronic coatings (available from 3M Company, St. Paul, Minn.), other fluorinated monomers for plasma-enhanced chemical vapor deposition (PECVD), and organosiloxane (e.g., SiOC) for PECVD. In some cases, the droplet operations surface may include a hydrophobic coating having a thickness ranging from about 10 nm to about 1,000 nm. Moreover, in some embodiments, the top substrate of the droplet actuator includes an electrically conducting organic polymer, which is then coated with a hydrophobic coating or otherwise treated to make the droplet operations surface hydrophobic. For example, the electrically conducting organic polymer that is deposited onto a plastic substrate may be poly(3,4-ethylenedioxythiophene) poly(styrenesulfonate) (PEDOT: PSS). Other examples of electrically conducting organic polymers and alternative conductive layers are described in Pollack et al., International Patent Application No. PCT/US2010/040705, entitled "Droplet Actuator Devices and Methods," the entire disclosure of which is incorporated herein by reference. One or both substrates may be fabricated using a printed circuit board (PCB), glass, indium tin oxide (ITO)-coated glass, and/or semiconductor materials as the substrate. When the substrate is ITO-coated glass, the ITO coating is preferably a thickness of at least about 20 nm, 50 nm, 75 nm, 100 nm or more. Alternatively or additionally the thickness can be at most about 200 nm, 150 nm, 125 nm or less. I In some cases, the top and/or bottom substrate includes a PCB substrate that is coated with a dielectric, such as a polyimide dielectric, which may in some cases also be coated or otherwise treated to make the droplet operations surface hydrophobic. When the substrate includes a PCB, the following materials are examples of suitable materials:

MITSUI™ BN-300 (available from MITSUI Chemicals America, Inc., San Jose, Calif.); ARLON™ 11N (available from Arlon, Inc, Santa Ana, Calif.).; NELCO® N4000-6 and N5000-30/32 (available from Park Electrochemical Corp., Melville, N.Y.); ISOLA™ FR406 (available from Isola Group, Chandler, Ariz.), especially IS620; fluoropolymer family (suitable for fluorescence detection since it has low background fluorescence); polyimide family; polyester; polyethylene naphthalate; polycarbonate; polyetheretherketone; liquid crystal polymer; cyclo-olefin copolymer (COC); cyclo-olefin polymer (COP); aramid; THERMOUNT® nonwoven aramid reinforcement (available from DuPont, Wilmington, Del.); NOMEX® brand fiber (available from DuPont, Wilmington, Del.); and paper. Various materials are also suitable for use as the dielectric component of the substrate. Examples include: vapor deposited dielectric, such as PARYLENE™ C (especially on glass), PARYLENE™ N, and PARYLENE™ HT (for high temperature, ~300° C.) (available from Parylene Coating Services, Inc., Katy, Tex.); TEFLON® AF coatings; cytop; soldermasks, such as liquid photoimageable soldermasks (e.g., on PCB) like TAIYO™ PSR4000 series, TAIYO™ PSR and AUS series (available from Taiyo America, Inc. Carson City, Nev.) (good thermal characteristics for applications involving thermal control), and PROBIMER™ 8165 (good thermal characteristics for applications involving thermal control (available from Huntsman Advanced Materials Americas Inc., Los Angeles, Calif.); dry film soldermask, such as those in the VACREL® dry film soldermask line (available from DuPont, Wilmington, Del.); film dielectrics, such as polyimide film (e.g., KAPTON® polyimide film, available from DuPont, Wilmington, Del.), polyethylene, and fluoropolymers (e.g., FEP), polytetrafluoroethylene; polyester; polyethylene naphthalate; cyclo-olefin copolymer (COC); cyclo-olefin polymer (COP); any other PCB substrate material listed above; black matrix resin; and polypropylene. Droplet transport voltage and frequency may be selected for performance with reagents used in specific assay protocols. Design parameters may be varied, e.g., number and placement of on-actuator reservoirs, number of independent electrode connections, size (volume) of different reservoirs, placement of magnets/bead washing zones, electrode size, inter-electrode pitch, and gap height (between top and bottom substrates) may be varied for use with specific reagents, protocols, droplet volumes, etc. In some cases, a substrate of the present disclosure may be derivatized with low surface-energy materials or chemistries, e.g., using deposition or in situ synthesis using poly- or per-fluorinated compounds in solution or polymerizable monomers. Examples include TEFLON® AF coatings and FLUOROPEL® coatings for dip or spray coating, other fluorinated monomers for plasma-enhanced chemical vapor deposition (PECVD), and organosiloxane (e.g., SiOC) for PECVD. Additionally, in some cases, some portion or all of the droplet operations surface may be coated with a substance for reducing background noise, such as background fluorescence from a PCB substrate. For example, the noise-reducing coating may include a black matrix resin, such as the black matrix resins available from Toray industries, Inc., Japan. Electrodes of a droplet actuator are typically controlled by a controller or a processor, which is itself provided as part of a system, which may include processing functions as well as data and software storage and input and output capabilities. Reagents may be provided on the droplet actuator in the droplet operations gap or in a reservoir fluidly coupled to the droplet operations gap. The reagents may be in liquid form, e.g., droplets, or they may be provided in a reconstitutable form in the droplet operations gap or in a reservoir fluidly coupled to the droplet operations gap. Reconstitutable reagents may typically be combined with liquids for reconstitution. An example of reconstitutable reagents suitable for use with the methods and apparatus described herein includes those described in Meathrel, et al., U.S. Pat. No. 7,727,466, entitled "Disintegratable films for diagnostic devices," granted on Jun. 1, 2010.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations that are sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to volume of the resulting droplets (i.e., the volume of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading. Droplet operations may be electrode-mediated. In some cases, droplet operations are further facilitated by the use of hydrophilic and/or hydrophobic regions on surfaces and/or by physical obstacles. For examples of droplet operations, see the patents and patent applications cited above under the definition of "droplet actuator." Impedance or capacitance sensing or imaging techniques may sometimes be used to determine or confirm the outcome of a droplet operation. Examples of such techniques are described in Sturmer et al., International Patent Pub. No. WO/2008/101194, entitled "Capacitance Detection in a Droplet Actuator," published on Aug. 21, 2008, the entire disclosure of which is incorporated herein by reference. Generally speaking, the sensing or imaging techniques may be used to confirm the presence or absence of a droplet at a specific electrode. For example, the presence of a dispensed droplet at the destination electrode following a droplet dispensing operation confirms that the droplet dispensing operation was effective. Similarly, the presence of a droplet at a detection spot at an appropriate step in an assay protocol may confirm that a previous set of droplet operations has successfully produced a droplet for detection. Droplet transport time can be quite fast. For example, in various embodiments, transport of a droplet from one electrode to the next may exceed about 1 sec, or about 0.1 sec, or about 0.01 sec, or about 0.001 sec. In one embodiment, the electrode is operated in AC mode but is switched to DC mode for imaging. It is helpful for conducting droplet operations for the footprint area of droplet to be similar to electrowetting area; in other words, 1×-, 2×- 3×-droplets are usefully controlled operated using 1, 2, and 3 electrodes, respectively. If the droplet footprint is greater than the number of electrodes available for conducting a droplet operation at a given time, the difference between the droplet size and the number of electrodes should typically not be greater than 1; in other words, a 2× droplet is usefully controlled using 1 electrode and a 3× droplet is usefully controlled using 2 electrodes. When droplets include beads, it is useful for droplet size to be equal to the number of electrodes controlling the droplet, e.g., transporting the droplet.

"Filler fluid" means a fluid, such as a gas or liquid, associated with a droplet operations substrate of a droplet actuator, which fluid is sufficiently immiscible with a droplet phase to render the droplet phase subject to electrode-mediated droplet operations. For example, the droplet operations gap of a droplet actuator is typically filled with a filler fluid. The filler fluid may, for example, be a low-viscosity oil, such as silicone oil or hexadecane filler fluid. The filler fluid may fill the entire gap of the droplet actuator or may coat one or more surfaces of the droplet actuator. Filler fluids may be conductive or non-conductive. Filler fluids may, for example, be doped with surfactants or other additives. For example, additives may be selected to improve droplet operations and/or reduce loss of reagent or target substances from droplets, formation of microdroplets, cross contamination between droplets, contamination of droplet actuator surfaces, degradation of droplet actuator materials, etc. Composition of the filler fluid, including surfactant doping, may be selected for performance with reagents used in the specific assay protocols and effective interaction or non-interaction with droplet actuator materials. Examples of filler fluids and filler fluid formulations suitable for use with the present disclosure are provided in Srinivasan et al, International Patent Pub. Nos. WO/2010/027894, entitled "Droplet Actuators, Modified Fluids and Methods," published on Mar. 11, 2010, and WO/2009/021173, entitled "Use of Additives for Enhancing Droplet Operations," published on Feb. 12, 2009; Sista et al., International Patent Pub. No. WO/2008/098236, entitled "Droplet Actuator Devices and Methods Employing Magnetic Beads," published on Aug. 14, 2008; and Monroe et al., U.S. Patent Publication No. 20080283414, entitled "Electrowetting Devices," filed on May 17, 2007; the entire disclosures of which are incorporated herein by reference, as well as the other patents and patent applications cited herein.

"Reservoir" means an enclosure or partial enclosure configured for holding, storing, or supplying liquid. A droplet actuator system of the present disclosure may include on-cartridge reservoirs and/or off-cartridge reservoirs. On-cartridge reservoirs may be (1) on-actuator reservoirs, which are reservoirs in the droplet operations gap or on the droplet operations surface; (2) off-actuator reservoirs, which are reservoirs on the droplet actuator cartridge, but outside the droplet operations gap, and not in contact with the droplet operations surface; or (3) hybrid reservoirs which have on-actuator regions and off-actuator regions. An example of an off-actuator reservoir is a reservoir in the top substrate. An off-actuator reservoir is typically in fluid communication with an opening or flow path arranged for flowing liquid from the off-actuator reservoir into the droplet operations gap, such as into an on-actuator reservoir. An off-cartridge reservoir may be a reservoir that is not part of the droplet actuator cartridge at all, but which flows liquid to some portion of the droplet actuator cartridge. For example, an off-cartridge reservoir may be part of a system or docking station to which the droplet actuator cartridge is coupled during operation. Similarly, an off-cartridge reservoir may be a reagent storage container or syringe which is used to force fluid into an on-cartridge reservoir or into a droplet operations gap. A system using an off-cartridge reservoir will typically include a fluid passage means whereby liquid may be transferred from the off-cartridge reservoir into an on-cartridge reservoir or into a droplet operations gap.

The terms "top," "bottom," "over," "under," and "on" are used throughout the description with reference to the relative positions of components of the droplet actuator, such as relative positions of top and bottom substrates of the droplet actuator. It will be appreciated that the droplet actuator is functional regardless of its orientation in space.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface. In one example, filler fluid can be considered as a film between such liquid and the electrode/array/matrix/surface.

When a droplet is described as being "on" or "loaded on" a droplet actuator, it should be understood that the droplet is arranged on the droplet actuator in a manner which facilitates using the droplet actuator to conduct one or more droplet operations on the droplet, the droplet is arranged on the droplet actuator in a manner which facilitates sensing of a property of or a signal from the droplet, and/or the droplet has been subjected to a droplet operation on the droplet actuator.

7 DESCRIPTION

The present disclosure provides a liquid handling system for supplying liquids to a flow cell. In one embodiment, the system is useful for performing sequencing reactions, such as SBS reactions. The present disclosure provides a droplet actuator that is used to supply liquids to the flow cell. Various electrode arrangements are provided in the droplet actuator for conducting droplet operations supplying liquids to a flow cell in a predetermined sequence. In certain embodiments, the LHS supports an external flow cell, and sequencing reactions are performed at the external flow cell. In other embodiments, rather than using an external flow cell, both the LHS and the flow cell for performing the sequencing reactions are integrated into the same droplet actuator.

Further, some embodiments utilize on-actuator reservoirs for supplying the various liquids of the LHS, while other embodiments utilize off-actuator, large-volume, gravity-driven dispensers for supplying the various liquids of the LHS.

FIG. 1 illustrates a top view of an example of an electrode arrangement 100 of a LHS for supplying liquids to a flow cell in a predetermined sequence. Electrode arrangement 100 is an electrode arrangement of a droplet actuator, such as the droplet actuator shown in FIG. 2. In this example, electrode arrangement 100 includes eight reservoir electrodes 110. Each of the reservoir electrodes 110 supports a corresponding on-actuator reservoir (now shown) of the droplet actuator (not shown). The on-actuator reservoirs of the droplet actuator are provided for storage of reagents, and may be "virtual electrodes." For example, in one non-limiting embodiment, each of the on-actuator reservoirs can store up to about 3 ml of liquid. Liquid atop the eight reservoir electrodes 110 can be dispensed in unit-sized droplets onto an arrangement of droplet operations electrodes 112 (i.e., electrowetting electrodes). More particularly, FIG. 1 shows that the eight reservoir electrodes 110 feed a loop 114 of droplet operations electrodes 112.

The loop 114 of droplet operations electrodes 112 is used to transfer droplets between each of the reservoir electrodes 110 and another arrangement of droplet operations electrodes 112. More particularly, FIG. 1 shows that the loop 114 of droplet operations electrodes 112 feeds a snakingsnaking path 116 of droplet operations electrodes 112, which serves as a delay line. Namely, the snaking path 116 of droplet operations electrodes 112 functions to accumulate a series of droplets for subsequent introduction into the flow cell (e.g., an external flow cell (not shown)). The snaking path 116 functions as a "cache" that accumulates and stores droplets between their source and the eventual destination. The order of the droplets within the snaking path 116 may be determined by software. For example, the order of the droplets may be 3 droplets of reagent A, followed by 10 droplets of reagent B, followed by 1 droplet of reagent C, and so on.

The end of snaking path 116 farthest from the loop 114 feeds a set of dedicated outlet electrodes 118 (e.g., a 3×3 or a 4×4 array of outlet electrodes 118). An opening 120 of the top substrate (not shown) of the droplet actuator is provided in close proximity to the outlet electrodes 118. The array of outlet electrodes 118 may be used to pool droplets before exiting the opening 120. Opening 120 may be provided in the top or bottom substrate, and/or in a side-wall of the droplet actuator. In one example, droplet operations electrodes 112 and outlet electrodes 118 are 2.25 mm squares that are designed to accommodate unit-droplets that are about 5 µl in volume. Depending on the specific application, many variations on (1) the type and number of reservoir electrodes 110, (2) the size of droplet operations electrodes 112 and outlet electrodes 118, (3) the cache size, and (4) the design of opening 120 can be envisioned. More details of electrode arrangement 100 implemented in a droplet actuator are described with reference to FIG. 2.

Figure 2:
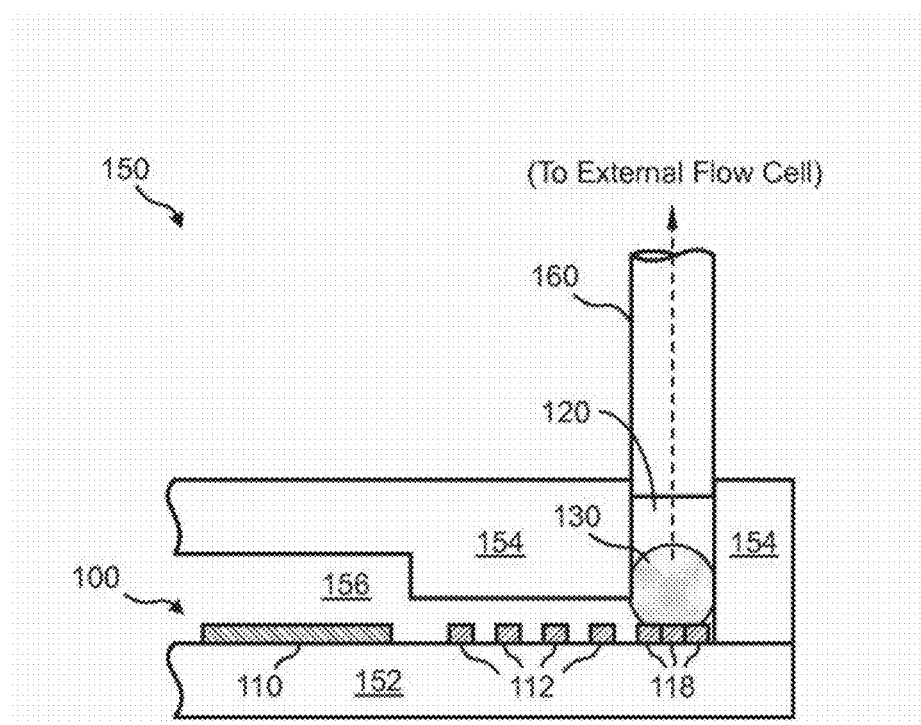
FIG. 2 illustrates a cross-sectional view of a portion of the electrode arrangement of FIG. 1 implemented in a droplet actuator.

FIG. 2 illustrates a cross-sectional view of a portion of electrode arrangement 100 of FIG. 1 implemented in a droplet actuator 150. More specifically, FIG. 2 is a cross-sectional view of a portion of electrode arrangement 100 taken along line A-A of FIG. 1. In this example, droplet actuator 150 includes a bottom substrate 152 and a top substrate 154 that are separated by a droplet operations gap 156. The droplet operations gap 156 is typically filled with a filler liquid (not shown). The filler liquid may, for example, be a low-viscosity oil, such as silicone oil or hexadecane filler liquid. Bottom substrate 152 includes electrode arrangement 100 of FIG. 1. More particularly, electrode arrangement 100 is on the side of bottom substrate 152 that is facing droplet operations gap 156. Top substrate 154 includes a conductive layer (not shown), which is on the side of top substrate 154 that is facing droplet operations gap 156. The conductive layer provides a ground reference plane with respect to electrode arrangement 100. Other layers (not shown), such as hydrophobic layers and dielectric layers, may be present on bottom substrate 152 and top substrate 154. A variety of electrode arrangements is possible, such as the strictly co-planar, substantially co-planar, bi-planar, and/or caternary wire configurations known in the art.

The height of droplet operations gap 156 (i.e., the gap height) may vary. For example, to accommodate reagent storage, the gap height at reservoir electrodes 110 is larger than the gap height at droplet operations electrodes 112, whereas the gap height at droplet operations electrodes 112 is set to facilitate droplet operations.

Top substrate 154 includes the opening 120 that is substantially aligned with outlet electrodes 118. FIG. 2 shows a tube 160 fitted into opening 120. Using tube 160, opening 120 is fluidly coupled to an inlet of an external flow cell (not shown). Namely, tube 160 provides a liquid flow path from the opening 120 of droplet actuator 150 to an external flow cell (not shown), wherein sequencing reactions are performed at the external flow cell. Opening 120 can take on a variety of different forms and configurations. For example, opening 120 is simply an opening in top substrate 154 that is connected to a tube (e.g., tube 160) or capillary which in turn is connected to the external flow cell.

A pump (not shown) provides negative pressure on the end of tube 160 at the flow cell, which causes liquid (e.g., liquid 130) to flow from outlet electrodes 118 through tube 160 and then through the flow cell. The control of the pump can be coordinated with the droplet operations performed on droplet actuator 150. In some cases, the pump may aspirate filler liquid between the delivery of each liquid reagent. In other cases, the presence of oil in the flow cell may be undesirable. In this case, care may need to be taken to avoid aspirating oil in between the delivery each liquid reagent. This could be achieved by ensuring that the amount aspirated is always slightly less than total volume available at opening 120, e.g., by careful matching of the volumetric flow-rates. Optionally, some form of feedback can be used to manage this process. For example, the impedance of the outlet electrodes 118 at opening 120 may be monitored during flow. As the liquid is withdrawn from droplet actuator 150 the footprint of the liquid on the array of outlet electrodes 118 shrinks until it is covering only a single outlet electrode 118. At this point, any further removal of liquid can be detected as a change in the impedance signature measured at the array of outlet electrodes 118. This in turn can be used as a trigger to stop the pump until additional liquid can be pooled at opening 120. Thus by using impedance sensing, the volume of liquid in opening 120 can be measured and then controlled to maintain a specific volume or to ensure that certain minimum or maximum thresholds are not exceeded.

In operation and referring now to FIGS. 1 and 2, using electrode arrangement 100, digital microfluidics (i.e., electrode-mediated or electrowetting-mediated droplet operations) is used to switch between the various liquids from the eight reservoir electrodes 110 as they are supplied to the flow cell in a predetermined sequence through the opening 120. Further, the supply of liquid from electrode arrangement 100 and through the flow cell may be punctuated. That is, there may be periods when the flow is stopped to enable reactions to occur inside the flow cell. During these periods the snaking path 116 of droplet operations electrodes 112 can be repopulated with a supply of droplets in preparation for the next flow cycle. If dispensing operations are considerably slower than transport operations, the cache of droplets may be beneficial in reducing the latency of droplets delivered to the opening 120. This is because the snaking path 116 of droplet operations electrodes 112 can be used to accumulate and position droplets while the flow is stopped. Using electrode arrangement 100, it is envisioned that the droplets within the cache march in a continual progression towards the opening 120.

In electrode arrangement 100, all of the droplets share a single droplet operations pathway between reservoir electrodes 110 and outlet electrodes 118. Therefore, electrode arrangement 100 is best suited for applications in which cross-contamination between droplets is not a concern. However, in applications in which the potential for cross-contamination between droplets is a concern other electrode arrangements are provided according to the present disclosure. For example, FIGS. 3, 4, and 5 show examples of electrode arrangements in which cross-contamination between droplets can be reduced or avoided.

Figure 3:
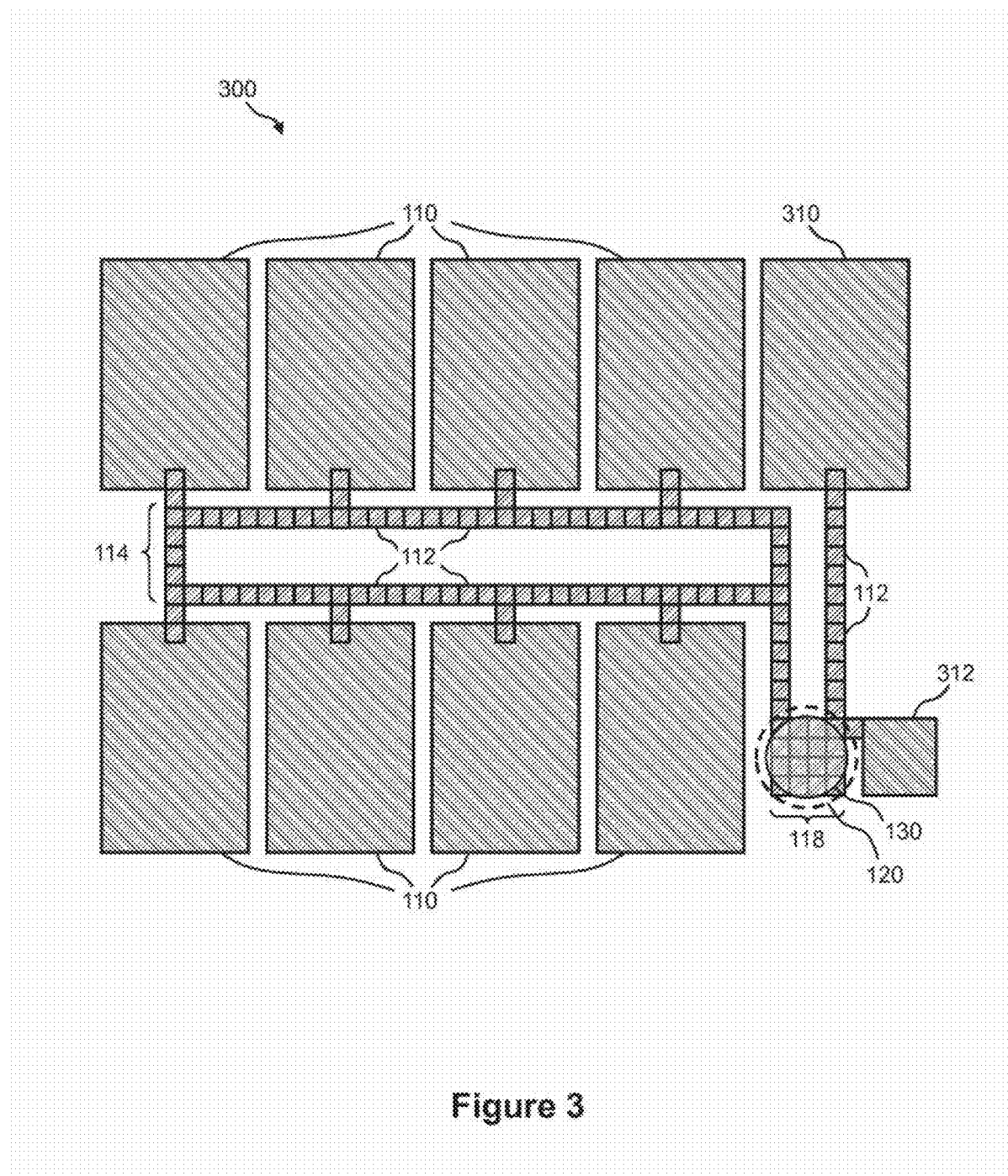
FIG. 3 illustrates a top view of another example of an electrode arrangement of a LHS for supplying liquids to a flow cell
Figure 4:
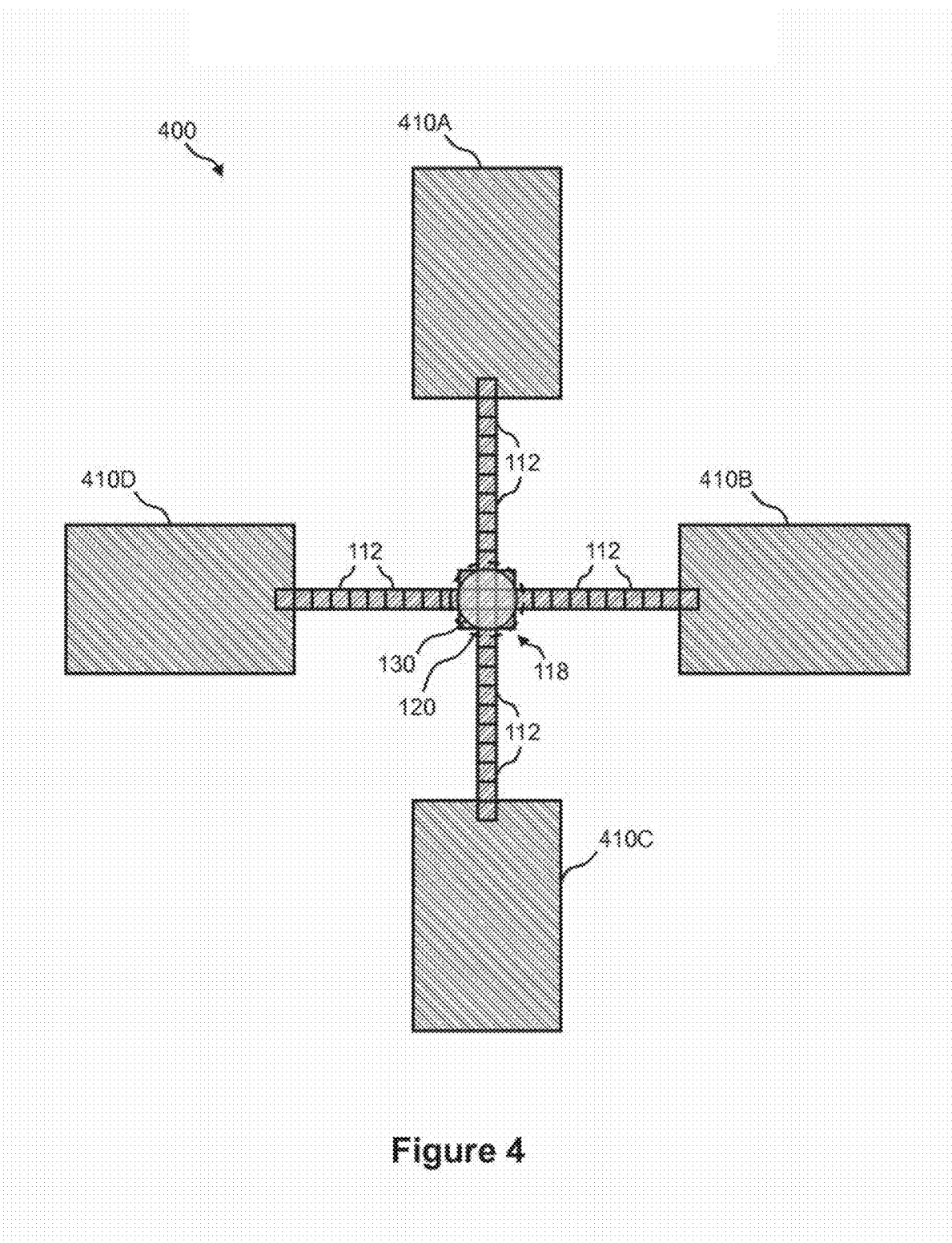
FIG. 4 illustrates a top view of yet another example of an electrode arrangement of a LHS for supplying liquids to a flow cell.

FIG. 3 illustrates a top view of another example of an electrode arrangement 300 of a LHS for supplying liquids to a flow cell in a predetermined sequence. Electrode arrangement 300 is an electrode arrangement of a droplet actuator, such as droplet actuator 150 of FIG. 2. In this example, electrode arrangement 300 supports one particular reagent reservoir that is segregated from other reagent reservoirs. Namely, electrode arrangement 300 is substantially the same as electrode arrangement 100 of FIG. 1, except that snaking path 116 of droplet operations electrodes 112 is omitted and replaced with a reservoir electrode 310 that feeds outlet electrodes 118 with its own dedicated arrangement of droplet operations electrodes 112. In this manner, the reagent liquid (not shown) stored at reservoir electrode 310 provides a dedicated pathway to outlet electrodes 118, whereas the reagent liquids of the other eight reservoir electrodes 110 share common pathways and storage structures.

Electrode arrangement 300 also includes a waste well 312 adjacent to outlet electrodes 118. The presence of waste well 312 adjacent to outlet electrodes 118 and opening 120 enables residual liquid from each cycle to be captured and removed from opening 120. Waste well 312 can also be used to capture "wash" droplets that are transported through the pathways between reagent droplets. A variety of waste well configurations are known in the art. These wash droplets are not intended to be inserted into the flow cell stream and are diverted into waste well 312 rather than into opening 120. Although electrode arrangement 300 supports eight reagents with common pathways and one reagent with a dedicated pathway, this allocation can be varied. For example, all nine reagents can have dedicated pathways.

Where dedicated pathways are required for each reagent, a variety of different architectures can be used. For example, FIGS. 4 and 5 show examples of radial architectures that have dedicated pathways.

FIG. 4 illustrates a top view of yet another example of an electrode arrangement 400 of a LHS for supplying liquids to a flow cell in a predetermined sequence. Electrode arrangement 400 is an electrode arrangement of a droplet actuator, such as droplet actuator 150 of FIG. 2. In this example, electrode arrangement 400 provides a radial architecture in which four reservoir electrodes 410 (e.g., reservoir electrodes 410A, 410B, 410C, and 410D) are arranged substantially equal distance from a 4×4 array of outlet electrodes 118. For example, if electrode arrangement 400 is analogized to a clock, reservoir electrode 410A is located at 12 o'clock, reservoir electrode 410B is located at 3 o'clock, reservoir electrode 410C is located at 6 o'clock, and reservoir electrode 410D is located at 9 o'clock. While FIG. 4 shows four reservoir electrodes 410 arranged radially with respect to outlet electrodes 118, this arrangement is exemplary only. Any number of reservoir electrodes 410 may be arranged around outlet electrodes 118 to the extent that there is sufficient installation space available.

Each of the reservoir electrodes 410 has its own dedicated arrangement of droplet operations electrodes 112 to outlet electrodes 118. Therefore, in this example, each of the reservoir electrodes 410 has an identical dedicated pathway for storing and transporting droplets to opening 120. As an alternative to forming and transporting individual unit-sized droplets, it is also possible to transport "slugs" of liquid 130 that span several droplet operations electrodes 112. For example, 5-10 droplet operations electrodes 112 in a line can be activated to convey a 5×-10× slug of liquid 130. As the flow rates required for sequencing can be quite high (e.g., up to 1 ml/min) compared to what is typically achieved using microfluidics it may be necessary to maximize the transfer of liquid 130 into the flow cell. Generally, this can be accomplished by moving droplets faster, moving larger droplets, and by reducing operational latencies. In one example, droplet operations electrodes 112 are 2.25 mm squares to be used with a gap height of about 1 mm and therefore carry unit-sized droplets approximately 5 µl in volume. Maximum transport switching rates of 5-10 Hz should be achievable which translates to about 8-17 µl/s (or about 0.4-0.8 ml/m) assuming that every third droplet operations electrode 112 is occupied by a droplet. When slugs of liquid 130 are used the flow rates can be even higher because fewer droplet operations electrodes 112 are unoccupied. For example, if 4× slugs of liquid 130 were used with two unoccupied droplet operations electrodes 112 between them, then the overall flow rate would be doubled (i.e., ⅔ occupancy versus ⅓ occupancy).

In electrode arrangement 400, the footprint of reservoir electrodes 410 is a rectangle shape. However, the reservoir electrodes can have other footprints, an example of which is shown in FIG. 5.

FIG. 5 illustrates a top view of still another example of an electrode arrangement 500 of a LHS for supplying liquids to a flow cell in a predetermined sequence. Electrode arrangement 500 is an electrode arrangement of a droplet actuator, such as droplet actuator 150 of FIG. 2. Electrode arrangement 500 provides a radial architecture and is substantially the same as electrode arrangement 400 of FIG. 4, except the rectangular-shaped reservoir electrodes 410 are replaced with circular-shaped reservoir electrodes 510.

FIGS. 6, 7, 8, and 9 illustrate top views of electrode arrangement 500 of FIG. 5 and a process of transporting liquid 130 to opening 120. More specifically, it is possible to directly transfer liquid 130 between each reservoir electrode 510 and opening 120 as shown in FIGS. 6, 7, 8, and 9. For example, a complete wetting path between a certain reservoir electrode 510 and opening 120 is created by energizing (i.e., turning on) all of the droplet operations electrodes 112 positioned between the two points.

Figure 6:
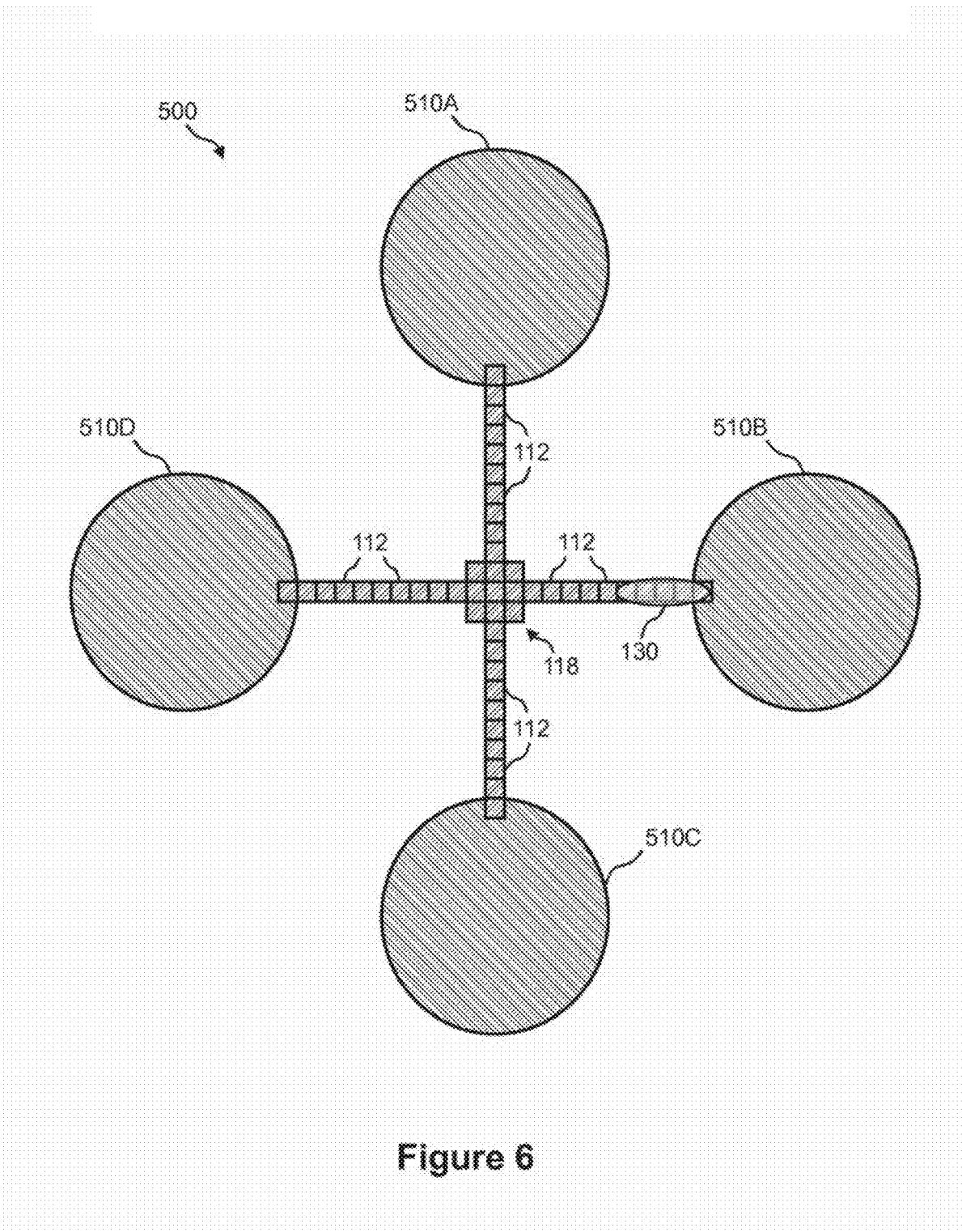
Figure 7:
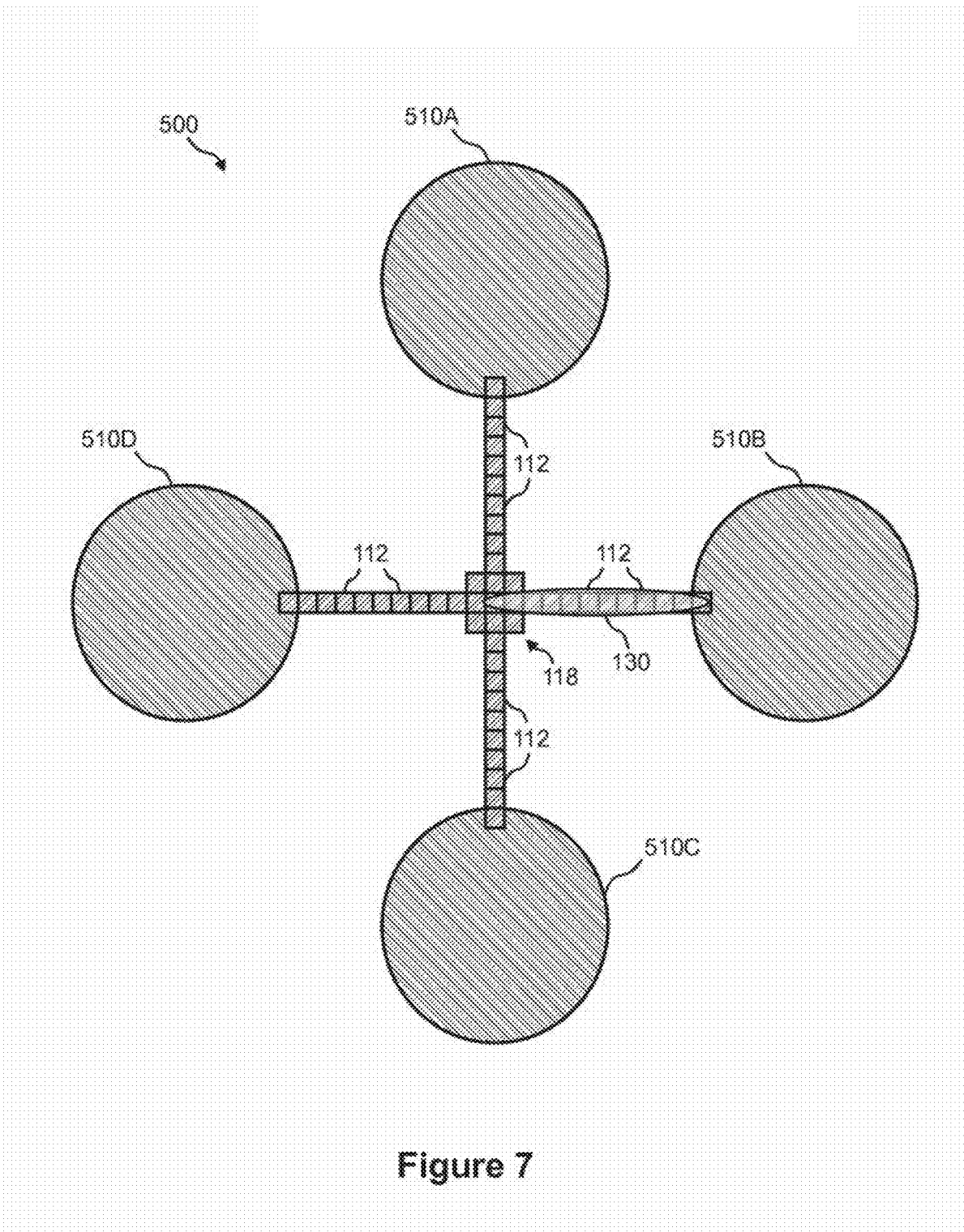
Figure 8:
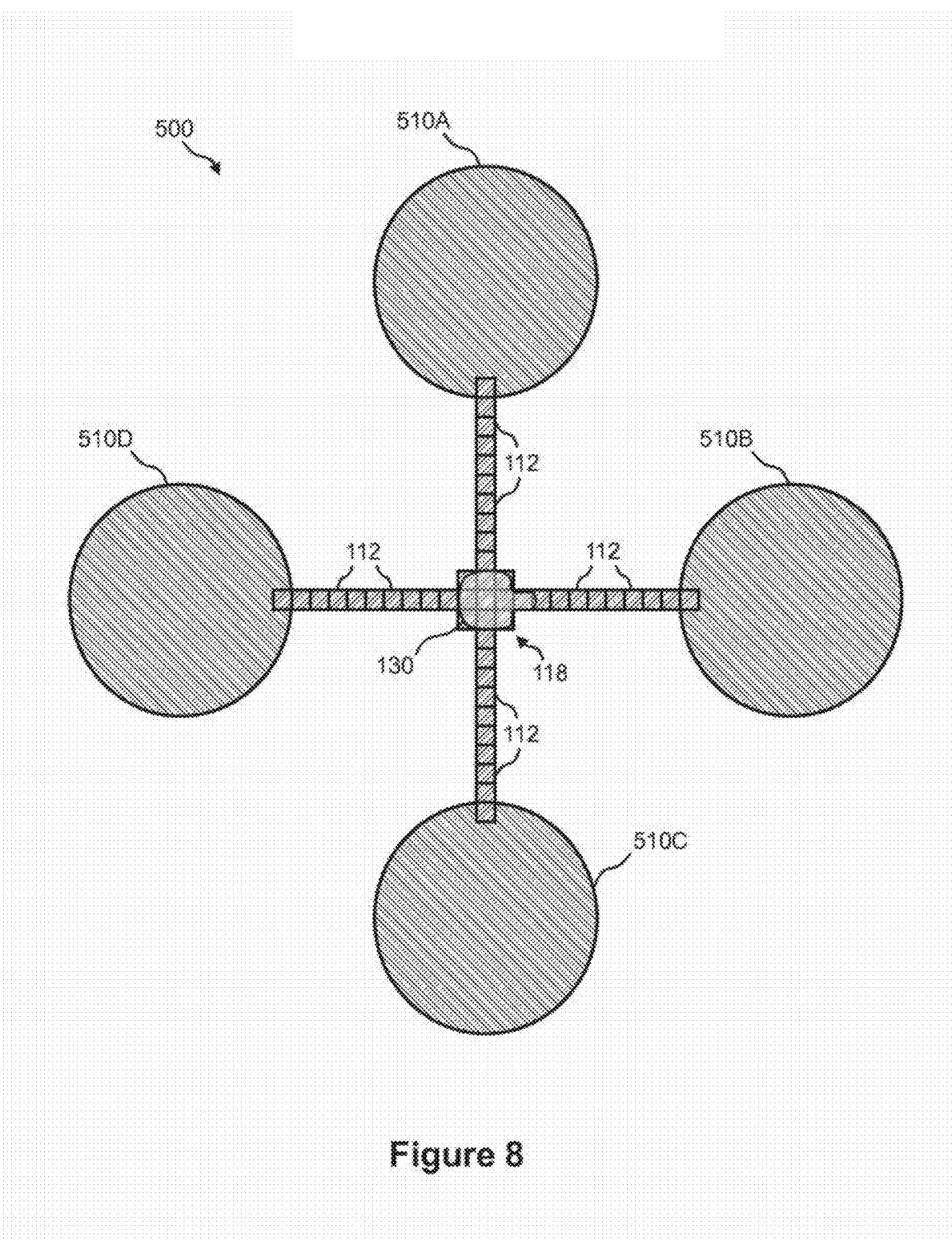
Figure 9:
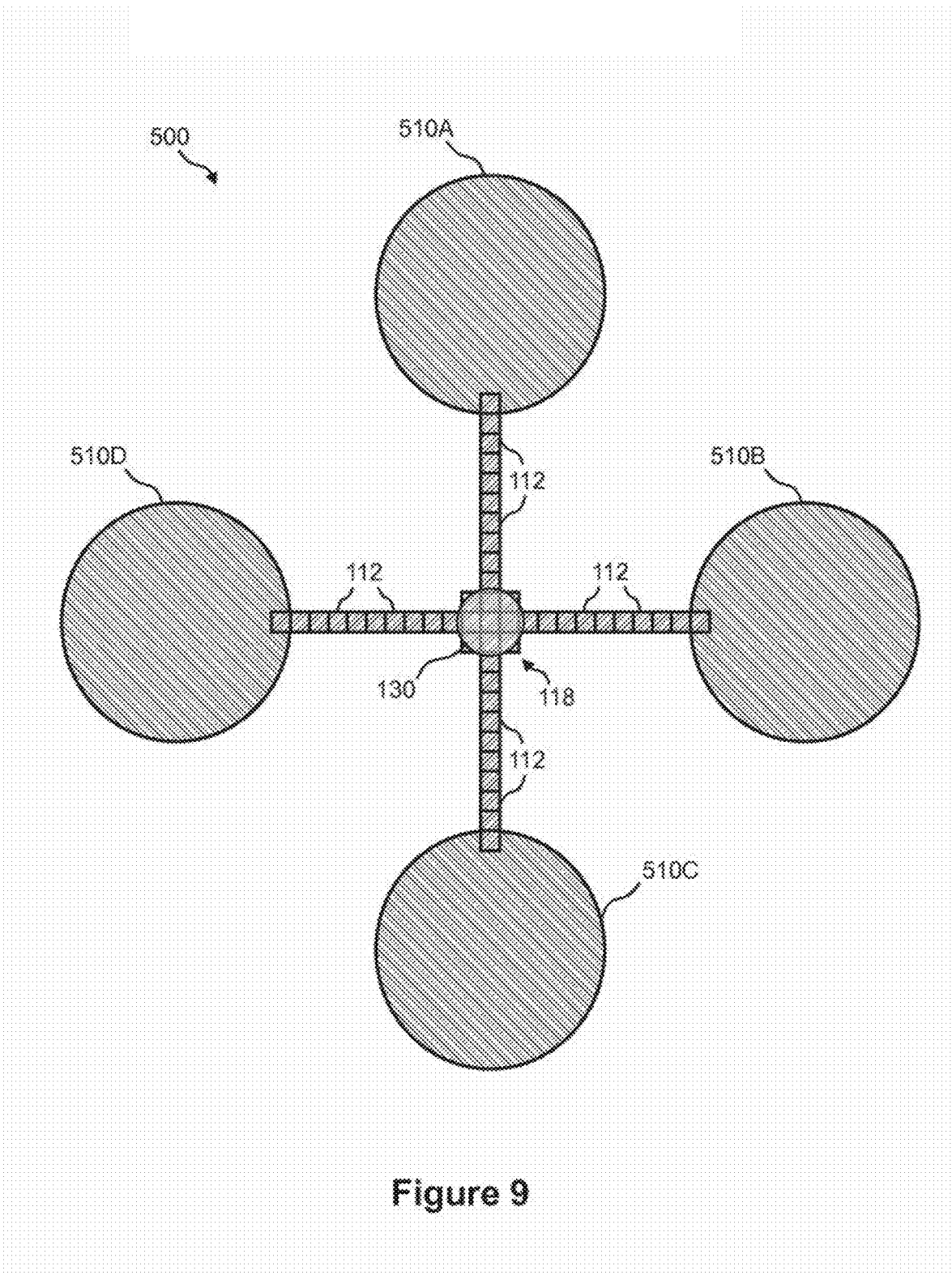

For example, FIG. 6 shows about five of the droplet operations electrodes 112 leading away from reservoir electrode 510B are turned on and an elongated 5× slug of liquid 130 begins to form toward outlet electrodes 118. Referring now to FIG. 7, all of the droplet operations electrodes 112 between reservoir electrode 510B and outlet electrodes 118 are turned on and an elongated 10× slug of liquid 130 now spans the full distance between reservoir electrode 510B and outlet electrodes 118. Referring now to FIGS. 8 and 9, the elongated slug of liquid 130 is transported onto outlet electrodes 118 by deactivating droplet operations electrodes 112 and activating outlet electrodes 118. This causes the slug of liquid 130 to be consolidated onto outlet electrodes 118 in a manner that is completely controlled. This radial architecture of, for example, electrode arrangements 400 and 500 may be most advantageous for applications in which high flow rates are required, as the radial architecture avoids the need to form and transport individual droplets. In such a case, the speed at which liquid 130 can be transferred may be limited only by the speed with which the contact line can advanced over the surface.

FIG. 10 illustrates another cross-sectional view of a portion of electrode arrangement 100 of FIG. 1, showing a gravity-driven, constant pressure, head dispenser (hereafter referred to as gravity-driven dispenser 1000) for delivering a large volume of liquid to the LHS, which is, for example, droplet actuator 150.

Because relatively large amounts of liquid are required to perform sequencing chemistry in a flow cell, it can be challenging to contain the liquids in a space-efficient manner. For example, in a typical on-actuator reservoir design, such as shown in droplet actuator 150 of FIG. 2, the gap height at the on-actuator reservoir is limited by several factors. For example, one limiting factor is that beyond a certain gap height contact is lost between the liquid and the conductive layer (not shown) of top substrate 154. Another limiting factor is that the force required to pull the liquid from the large gap height at reservoir electrodes 110 into the small gap height at the droplet operations electrodes 112 becomes too great. Generally, the capacity of on-actuator reservoirs is increased by keeping the gap height fixed, but making the area larger. Up to several ml of liquid can be conveniently stored in on-actuator reservoirs with the primary limitation being that they consume a great deal of real estate on the droplet actuator.

However, in order to reduce the amount of real estate that is dedicated to storing reagent liquid in the LHS of the present disclosure, gravity-driven dispensers 1000 can be utilized in place of or feeding the on-actuator reservoirs. Gravity-driven dispenser 1000 includes a vessel 1010, which is sized to hold a certain volume of liquid, such as liquid 1016. Vessel 1010 may be, for example, a cylinder-shaped tube in which one end is funnel-shaped. The large end of vessel 1010 is enclosed. An outlet 1012 is provided at the narrow end of the funnel-shaped portion of vessel 1010. In its simplest form, outlet 1012 may be a hole or opening. Additionally, outlet 1012 may be a hole feeding a tube. An inlet 1014 is provided along the side of vessel 1010. In its simplest form, inlet 1014 may be a hole or opening. Additionally, inlet 1014 may be a hole feeding a tube. In one example, gravity-driven dispenser 1000 is based on the gravity-driven dispenser described with referent to International Patent App. No. PCT/US12/55769, entitled "Microfluidic loading apparatus and methods," filed on Sep. 17, 2012, the entire disclosure of which is incorporated herein by reference.

In gravity-driven dispenser 1000, vessel 1010 holds a column of liquid 1016. Vessel 1010 opens to atmosphere through inlet 1014. Inlet 1014 is a hydrophobic pore at a defined height from outlet 1012. This configuration reduces the head pressure which is also kept constant as long as the liquid level is higher than inlet 1014. The size of the column is limited by the burst pressure of inlet 1014. This configuration is well-suited for, among other things, applications in which a large volume of liquid needs to be contained within a reasonably small footprint.

In operation, gravity-driven dispenser 1000 is filled with a certain amount of liquid 1016, such as reagent liquid. Inlet 1014 serves as a vent for allowing air to enter vessel 1010. For example, FIG. 10 shows air bubbles 1018 entering vessel 1010 through inlet 1014. As air bubbles 1018 displace liquid 1016 in vessel 1010, droplets of liquid 1016 are dispensed from outlet 1012.

In the example of electrode arrangement 100, there is one gravity-driven dispenser 1000 supporting each of the reservoir electrodes 110. For example, if there are eight reservoir electrodes 110, then there are eight gravity-driven dispensers 1000 associated with electrode arrangement 100.

In FIGS. 1 through 10, the LHSs supply liquid to a flow cell that is located external to the droplet actuator, such as external to droplet actuator 150. However, it is also possible to directly integrate the flow cell into the droplet actuator. FIGS. 11A, 11B, and 11C illustrate top views of examples of electrode arrangements for performing sequencing reactions within the droplet actuator rather than in an external flow cell. Namely, rather than using an external flow cell, the electrode arrangements of FIGS. 11A, 11B, and 11C allow both the LHS and the flow cell for performing the sequencing reactions to be integrated into the same droplet actuator.

For example, FIGS. 11A, 11B, and 11C show an electrode arrangement 1100 that includes an arrangement of droplet operations electrodes 1110, which provides one or more surfaces with which liquid interacts to perform the sequencing reaction in a droplet actuator. In one example, electrode arrangement 1100 includes droplet operations electrodes 1110A, 1110B, and 1110C, wherein droplet operations electrode 1110B is the surface with which liquid interacts to perform the sequencing reaction. Namely, droplet operations electrode 1110B provides a specialized area in the droplet actuator to support the sequencing chemistry. A droplet actuator typically requires a hydrophobic surface for operation while sequencing surfaces are typically hydrophilic owing to the presence of large amounts of DNA. Thus it is challenging to support both LHS processes and sequencing processes simultaneously on the same surface. Any sequencing areas wetted using droplet operations will likely remain wetted and liquid exchange must occur by mixing or diluting the residual liquid with fresh liquid each time. This can be performed by simply adding liquid at one side of the electrode while removing liquid from the other side, as is frequently done for washing of paramagnetic beads using droplet operations. Using this approach, the surface area of droplet operations electrodes 1110 are made hydrophobic to support LHS processes, while a portion of the one or more droplet operations electrodes 1110 is made hydrophilic to support sequencing chemistry. For example, the surface of the droplet operations electrode 1110B is first coated with a hydrophobic coating. Then, a portion of droplet operations electrode 1110B is coated with a hydrophilic coating to form a hydrophilic spot 1112 atop droplet operations electrode 1110B. By maintaining a certain size or fractional area of the droplet operations electrode 1110B it is possible to remove the bulk of the liquid by transferring it to the adjacent droplet operations electrode 1110. While the hydrophilic spot 1112 will retain some water, the bulk of the droplet can be transported across the surface enabling very rapid liquid exchange.

Referring now to FIG. 11A, the hydrophilic spot 1112 is present atop droplet operations electrode 1110B. In this example, the hydrophilic spot 1112 has the same square footprint as droplet operations electrode 1110B, but has a slightly smaller dimension leaving the edge of droplet operations electrode 1110B exposed. Referring now to FIG. 11B, again the hydrophilic spot 1112 is present atop droplet operations electrode 1110B. In this example, the hydrophilic spot 1112 has a circular footprint whereas droplet operations electrode 1110B has a square footprint. As a result, a larger portion of droplet operations electrode 1110B is left exposed as compared with FIG. 11A. Referring now to FIG. 11C, multiple small hydrophilic spots 1112 are present atop droplet operations electrode 1110B. As a result, portions of droplet operations electrode 1110B are left exposed between the multiple small hydrophilic spots 1112.

With the flow cell integrated into the droplet actuator, it is possible to perform a sample-to-sequence protocol. As DNA sequencing is currently quite complex to perform, there is a need for more robust and automated devices that would enable non-expert users to generate and interpret genetic information obtained by DNA sequencing. This would enable DNA sequencing to be more routinely applied to clinical and applied problems. Additionally, the integration of a flow cell into a droplet actuator would enable massively parallel sequencing to be performed.

A particularly useful application of the apparatus and methods set forth herein is nucleic acid sequencing, such as a sequencing-by-synthesis (SBS) technique. Briefly, SBS can be initiated by contacting a target nucleic acid with one or more labeled nucleotides, DNA polymerase, etc. One or more different species of target nucleic acids can be attached to a hydrophilic surface or other solid phase substrate set forth herein and reagents can be delivered to the one or more target nucleic acids using the droplet manipulation steps set forth herein. For example, different species of target nucleic acids can be attached at different features on the surface or substrate. Those features where a primer is extended using the target nucleic acid as template will incorporate a labeled nucleotide that can be detected. Optionally, the labeled nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures, detection platforms that can be readily adapted for use with an apparatus or method of the present disclosure are described, for example, in Bentley et al., *Nature* 456: 53-59 (2008), WO 04/018497; WO 91/06678; WO 07/123744; U.S. Pat. Nos. 7,057,026; 7,329,492; 7,211,414; 7,315,019 or 7,405,281, and US Pat. App. Pub. No. 2008/0108082 A1, each of which is incorporated herein by reference.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., *Analytical Biochemistry* 242(1), 84-9 (1996); Ronaghi, *Genome Res.* 11(1), 3-11 (2001); Ronaghi et al. *Science* 281(5375), 363 (1998); U.S. Pat. Nos. 6,210,891; 6,258,568 and 6,274,320, each of which is incorporated herein by reference). In pyrosequencing, released PPi can be detected by being converted to adenosine triphosphate (ATP) by ATP sulfurylase, and the resulting ATP can be detected via luciferase-produced photons. Thus, the sequencing reaction can be monitored via a luminescence detection system. Excitation radiation sources used for fluorescence based detection systems are not necessary for pyrosequencing procedures. Useful detectors and procedures that can be used for application of pyrosequencing to arrays of the present disclosure are described, for example, in WIPO Pat. App. Ser. No. PCT/US11/57111, US Pat. App. Pub. No. 2005/0191698 A1, U.S. Pat. No. 7,595,883, and U.S. Pat. No. 7,244,559, each of which is incorporated herein by reference.

Sequencing-by-ligation reactions are also useful including, for example, those described in Shendure et al. *Science* 309:1728-1732 (2005); U.S. Pat. No. 5,599,675; and U.S. Pat. No. 5,750,341, each of which is incorporated herein by reference. Some embodiments can include sequencing-by-hybridization procedures as described, for example, in Bains et al., *Journal of Theoretical Biology* 135(3), 303-7 (1988); Drmanac et al., *Nature Biotechnology* 16, 54-58 (1998); Fodor et al., *Science* 251(4995), 767-773 (1995); and WO 1989/10977, each of which is incorporated herein by reference. In both sequencing-by-ligation and sequencing-by-hybridization procedures, nucleic acids that are present on a solid support or hydrophilic surface are subjected to repeated cycles of oligonucleotide delivery and detection. Typically, the oligonucleotides are fluorescently labeled and can be detected using fluorescence detectors similar to those described with regard to SBS procedures herein or in references cited herein.

Some embodiments can utilize methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zeromode waveguides. Techniques and reagents for FRET-based sequencing are described, for example, in Levene et al. *Science* 299, 682-686 (2003); Lundquist et al. *Opt. Lett.* 33, 1026-1028 (2008); Korlach et al. *Proc. Natl. Acad. Sci. USA* 105, 1176-1181 (2008), the disclosures of which are incorporated herein by reference.

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in US Pat. App. Pub. Nos. 2009/0026082 A1; 2009/0127589 A1; 2010/0137143 A1; or 2010/0282617 A1, each of which is incorporated herein by reference.

Another useful application for an array of the present disclosure is gene expression analysis. Gene expression can be detected or quantified using RNA sequencing techniques, such as those, referred to as digital RNA sequencing. RNA sequencing techniques can be carried out using sequencing methodologies known in the art such as those set forth above. Gene expression can also be detected or quantified using hybridization techniques carried out by direct hybridization to an array or using a multiplex assay, the products of which are detected on an array. Such an array can be present at a hydrophilic surface or other solid support set forth herein. An array can also be used to determine genotypes for a genomic DNA sample from one or more individual. Exemplary methods for array-based expression and genotyping analysis that can be carried out using a method or apparatus of the present disclosure are described in U.S. Pat. Nos. 7,582,420; 6,890,741; 6,913,884 or 6,355,431 or US Pat. App. Pub. Nos. 2005/0053980 A1; 2009/0186349 A1 or 2005/0181440 A1, each of which is incorporated herein by reference.

Nucleic acids can be attached to a hydrophilic surface and amplified to form a colonies or clusters. A colony or cluster is a type of array feature. Clusters can be created by solid-phase amplification methods. For example, a nucleic acid having one or more template sequences to be detected can be attached to a surface and amplified using bridge amplification. Useful bridge amplification methods are described, for example, in U.S. Pat. No. 5,641,658; U.S. Patent Publ. No. 2002/0055100; U.S. Pat. No. 7,115,400; U.S. Patent Publ. No. 2004/0096853; U.S. Patent Publ. No. 2004/0002090; U.S. Patent Publ. No. 2007/0128624; and U.S. Patent Publ. No. 2008/0009420, each of which is incorporated herein by reference. Another useful method for amplifying nucleic acids on a surface is rolling circle amplification (RCA), for example, as described in Lizardi et al., *Nat. Genet.* 19:225-232 (1998) and US Pat. App. Pub. No. 2007/0099208 A1, each of which is incorporated herein by reference. Another type of array that is useful is an array of particles produced from an emulsion PCR amplification technique. Examples are described in Dressman et al., *Proc. Natl. Acad. Sci. USA* 100:8817-8822 (2003), WO 05/010145, US 2005/0130173 or US 2005/0064460, each of which is incorporated herein by reference.

Several applications for arrays have been exemplified above in the context of ensemble detection, wherein multiple copies of a target nucleic acid are present at each feature and are detected together. In alternative embodiments, a single nucleic acid, whether a target nucleic acid or amplicon thereof, can be detected at each feature. For example, a feature on a hydrophilic surface can be configured to contain a single nucleic acid molecule having a target nucleotide sequence that is to be detected. Any of a variety of single molecule detection techniques can be used including, for example, modifications of the ensemble detection techniques set forth above to detect the sites at increased resolution or using more sensitive labels. Other examples of single molecule detection methods that can be used are set forth in US Pat. App. Pub. No. 2011/0312529 A1; U.S. Ser. No. 61/578,684; and U.S. Ser. No. 61/540,714, each of which is incorporated herein by reference.

7.1 Systems

FIG. 12 illustrates a functional block diagram of an example of a microfluidics system 1200 that includes a droplet actuator 1205. Digital microfluidic technology conducts droplet operations on discrete droplets in a droplet actuator, such as droplet actuator 1205, by electrical control of their surface tension (electrowetting). The droplets may be sandwiched between two substrates of droplet actuator 1205, a bottom substrate and a top substrate separated by a droplet operations gap. The bottom substrate may include an arrangement of electrically addressable electrodes. The top substrate may include a reference electrode plane made, for example, from conductive ink or indium tin oxide (ITO). The bottom substrate and the top substrate may be coated with a hydrophobic material. Droplet operations are conducted in the droplet operations gap. The space around the droplets (i.e., the gap between bottom and top substrates) may be filled with an immiscible inert liquid, such as silicone oil, to prevent evaporation of the droplets and to facilitate their transport within the device. Other droplet operations may be effected by varying the patterns of voltage activation; examples include merging, splitting, mixing, and dispensing of droplets.

Droplet actuator 1205 may be designed to fit onto an instrument deck (not shown) of microfluidics system 1200. The instrument deck may hold droplet actuator 1205 and house other droplet actuator features, such as, but not limited to, one or more magnets and one or more heating devices. For example, the instrument deck may house one or more magnets 1210, which may be permanent magnets. Optionally, the instrument deck may house one or more electromagnets 1215. Magnets 1210 and/or electromagnets 1215 are positioned in relation to droplet actuator 1205 for immobilization of magnetically responsive beads. Optionally, the positions of magnets 1210 and/or electromagnets 1215 may be controlled by a motor 1220. Additionally, the instrument deck may house one or more heating devices 1225 for controlling the temperature within, for example, certain reaction and/or washing zones of droplet actuator 1205. In one example, heating devices 1225 may be heater bars that are positioned in relation to droplet actuator 1205 for providing thermal control thereof.

A controller 1230 of microfluidics system 1200 is electrically coupled to various hardware components of the present disclosure, such as droplet actuator 1205, electromagnets 1215, motor 1220, and heating devices 1225, as well as to a detector 1235, an impedance sensing system 1240, and any other input and/or output devices (not shown). Controller 1230 controls the overall operation of microfluidics system 1200. Controller 1230 may, for example, be a general purpose computer, special purpose computer, personal computer, or other programmable data processing apparatus. Controller 1230 serves to provide processing capabilities, such as storing, interpreting, and/or executing software instructions, as well as controlling the overall operation of the system. Controller 1230 may be configured and programmed to control data and/or power aspects of these devices. For example, in one aspect, with respect to droplet actuator 1205, controller 1230 controls droplet manipulation by activating/deactivating electrodes.

In one example, detector 1235 may be an imaging system that is positioned in relation to droplet actuator 1205. In one example, the imaging system may include one or more light-emitting diodes (LEDs) (i.e., an illumination source) and a digital image capture device, such as a charge-coupled device (CCD) camera. Detection can be carried out using an apparatus suited to a particular reagent or label in use. For example, an optical detector such as a fluorescence detector, absorbance detector, luminescence detector or the like can be used to detect appropriate optical labels. Systems designed for array-based detection are particularly useful. For example, optical systems for use with the methods set forth herein may be constructed to include various components and assemblies as described in U.S. Pat. Nos. 8,241,573; 7,329,860 and 8,039,817; and US Pat. App. Pub. Nos. 2009/0272914 A1 and 2012/0270305 A1, each of which is incorporated herein by reference. Such detection systems are particularly useful for nucleic acid sequencing embodiments.

Impedance sensing system 1240 may be any circuitry for detecting impedance at a specific electrode of droplet actuator 1205. In one example, impedance sensing system 1240 may be an impedance spectrometer. Impedance sensing system 1240 may be used to monitor the capacitive loading of any electrode, such as any droplet operations electrode, with or without a droplet thereon. For examples of suitable capacitance detection techniques, see Sturmer et al., International Patent Publication No. WO/2008/101194, entitled "Capacitance Detection in a Droplet Actuator," published on Aug. 21, 2008; and Kale et al., International Patent Publication No. WO/2002/080822, entitled "System and Method for Dispensing Liquids," published on Oct. 17, 2002; the entire disclosures of which are incorporated herein by reference.

Droplet actuator 1205 may include disruption device 1245. Disruption device 1245 may include any device that promotes disruption (lysis) of materials, such as tissues, cells and spores in a droplet actuator. Disruption device 1245 may, for example, be a sonication mechanism, a heating mechanism, a mechanical shearing mechanism, a bead beating mechanism, physical features incorporated into the droplet actuator 1205, an electric field generating mechanism, a thermal cycling mechanism, and any combinations thereof. Disruption device 1245 may be controlled by controller 1230.

It will be appreciated that various aspects of the present disclosure may be embodied as a method, system, computer readable medium, and/or computer program product. Aspects of the present disclosure may take the form of hardware embodiments, software embodiments (including firmware, resident software, micro-code, etc.), or embodiments combining software and hardware aspects that may all generally be referred to herein as a "circuit," "module" or "system." Furthermore, the methods of the present disclosure may take the form of a computer program product on a computer-usable storage medium having computer-usable program code embodied in the medium.

Any suitable computer useable medium may be utilized for software aspects of the present disclosure. The computer-usable or computer-readable medium may be, for example but not limited to, an electronic, magnetic, optical, electromagnetic, infrared, or semiconductor system, apparatus, device, or propagation medium. The computer readable medium may include transitory and/or non-transitory embodiments. More specific examples (a non-exhaustive list) of the computer-readable medium would include some or all of the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission medium such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device.

Program code for carrying out operations of the present disclosure may be written in an object oriented programming language such as Java, Smalltalk, C++ or the like. However, the program code for carrying out operations of the present disclosure may also be written in conventional procedural programming languages, such as the "C" programming language or similar programming languages. The program code may be executed by a processor, application specific integrated circuit (ASIC), or other component that executes the program code. The program code may be simply referred to as a software application that is stored in memory (such as the computer readable medium discussed above). The program code may cause the processor (or any processor-controlled device) to produce a graphical user interface ("GUI"). The graphical user interface may be visually produced on a display device, yet the graphical user interface may also have audible features. The program code, however, may operate in any processor-controlled device, such as a computer, server, personal digital assistant, phone, television, or any processor-controlled device utilizing the processor and/or a digital signal processor.

The program code may locally and/or remotely execute. The program code, for example, may be entirely or partially stored in local memory of the processor-controlled device. The program code, however, may also be at least partially remotely stored, accessed, and downloaded to the processor-controlled device. A user's computer, for example, may entirely execute the program code or only partly execute the program code. The program code may be a stand-alone software package that is at least partly on the user's computer and/or partly executed on a remote computer or entirely on a remote computer or server. In the latter scenario, the remote computer may be connected to the user's computer through a communications network.

The present disclosure may be applied regardless of networking environment. The communications network may be a cable network operating in the radio-frequency domain and/or the Internet Protocol (IP) domain. The communications network, however, may also include a distributed computing network, such as the Internet (sometimes alternatively known as the "World Wide Web"), an intranet, a local-area network (LAN), and/or a wide-area network (WAN). The communications network may include coaxial cables, copper wires, fiber optic lines, and/or hybrid-coaxial lines. The communications network may even include wireless portions utilizing any portion of the electromagnetic spectrum and any signaling standard (such as the IEEE 802 family of standards, GSM/CDMA/TDMA or any cellular standard, and/or the ISM band). The communications network may even include powerline portions, in which signals are communicated via electrical wiring. The present disclosure may be applied to any wireless/wireline communications network, regardless of physical componentry, physical configuration, or communications standard(s).

Certain aspects of present disclosure are described with reference to various methods and method steps. It will be understood that each method step can be implemented by the program code and/or by machine instructions. The program code and/or the machine instructions may create means for implementing the functions/acts specified in the methods.

The program code may also be stored in a computer-readable memory that can direct the processor, computer, or other programmable data processing apparatus to function in a particular manner, such that the program code stored in the computer-readable memory produce or transform an article of manufacture including instruction means which implement various aspects of the method steps.

The program code may also be loaded onto a computer or other programmable data processing apparatus to cause a series of operational steps to be performed to produce a processor/computer implemented process such that the program code provides steps for implementing various functions/acts specified in the methods of the present disclosure.

8 CONCLUDING REMARKS

The foregoing detailed description of embodiments refers to the accompanying drawings, which illustrate specific embodiments of the present disclosure. Other embodiments having different structures and operations do not depart from the scope of the present disclosure. The term "the present disclosure" or the like is used with reference to certain specific examples of the many alternative aspects or embodiments of the applicants' present disclosure set forth in this specification, and neither its use nor its absence is intended to limit the scope of the applicants' present disclosure or the scope of the claims. This specification is divided into sections for the convenience of the reader only. Headings should not be construed as limiting of the scope of the present disclosure. The definitions are intended as a part of the description of the present disclosure. It will be understood that various details of the present disclosure may be changed without departing from the scope of the present disclosure. Furthermore, the foregoing description is for the purpose of illustration only, and not for the purpose of limitation.

I claim:

1. A digital microfluidic liquid handling system, comprising:
   liquid reservoirs;
   a droplet actuator, comprising:
      a bottom substrate separated from a top substrate to form a droplet operations gap, wherein the droplet operations gap is filled with a filler fluid, and wherein the top substrate includes an opening;
      reservoir electrodes disposed on the bottom substrate, wherein each reservoir electrode corresponds with a respective one of the liquid reservoirs;
      outlet electrodes disposed on the bottom substrate and arranged proximal to the opening;
      droplet operations electrodes defining a path between the reservoir electrodes and the outlet electrodes; and
      a flow cell fluidly coupled to the droplet operations gap through the opening in the top substrate, said flow cell being external with respect to the droplet actuator;
   wherein said liquid reservoirs being external reservoirs fluidly coupled to the droplet operations gap through a second opening in one of the bottom substrate or top substrate.

2. The system of claim 1 wherein each of the external reservoirs comprises a gravity-driven liquid dispenser.

3. The system of claim 1 wherein a portion of the droplet operations electrodes form a loop that is fluidly connected to each of the reservoir electrodes, and an other portion of the droplet operations electrodes form a snaking path that is fluidly connected to the outlet electrodes, and wherein the snaking path is to provide a cache for accumulating and storing droplets between their source and destination.

4. The system of claim 3 wherein a conductive layer is disposed on the top substrate.

5. The system of claim 4 wherein the conductive layer is disposed on a side of the top substrate that is facing the droplet operations gap.

6. The system of claim 4 wherein the conductive layer is configured as a ground reference plane with respect to the reservoir electrodes, the droplet operations electrodes, and the outlet electrodes.

7. The system of claim 1 wherein a height of the droplet operations gap varies.

8. The system of claim 7 wherein the height of the droplet operations gap at the reservoir electrodes is greater than the height of the droplet operations gap at the droplet operations electrodes.

9. The system of claim 1 wherein the opening is fluidly coupled to an inlet of the flow cell via a tube and further comprising a pump for providing negative pressure on an end of the tube at the flow cell and causing liquid to flow from the outlet electrodes through the opening and through the tube and then through the flow cell.

10. The system of claim 1 wherein one of the liquid reservoirs corresponds with one of the reservoir electrodes, and wherein the one of the reservoir electrodes feeds the outlet electrodes with a dedicated arrangement of the droplet operations electrodes, and wherein a remainder of the liquid reservoirs and their corresponding reservoir electrodes share a common pathway of the droplet operations electrodes that is separate from the dedicated arrangement of the droplet operations electrodes.

11. The system of claim 1 wherein the reservoir electrodes are arranged radially with respect to the outlet electrodes and wherein dedicated arrangements of the droplet operations electrodes connect each reservoir electrode with the outlet electrodes.

12. The system of claim 2 wherein the gravity-driven liquid dispenser comprises a vessel; an outlet; and an inlet at a defined height from the outlet.

13. The system of claim 12 wherein the inlet comprises a hydrophobic pore.

14. The system of claim 12 wherein the outlet is fluidly coupled to the droplet operations gap and aligned with the corresponding reservoir electrode.

15. The system of claim 1 wherein the flow cell is integrated into the droplet actuator and wherein the reservoir electrodes, the droplet operations electrodes, and the outlet electrodes have surfaces that comprise one or more hydrophilic spots.

16. A method of supplying liquids to a flow cell using a digital microfluidic liquid handling system, comprising:
   dispensing one or more droplets from a liquid reservoir onto a reservoir electrode corresponding with the liquid reservoir;
   transferring the one or more droplets from the reservoir electrode to outlet electrodes along a pathway defined by droplet operations electrodes;
   transferring the one or more droplets from the outlet electrodes through an opening arranged proximal thereto and into a flow cell in a predetermined sequence;
   monitoring an impedance at the outlet electrodes during flow of the one or more droplets;
   detecting a change in the impedance in response to the transfer of the one or more droplets from the outlet electrodes; and
   in response to the detecting, stopping a pump used to transfer the one or more droplets from the outlet electrodes until additional droplets are pooled at the outlet electrodes.

17. The method of claim 16 wherein the transferring of the one or more droplets along the pathway includes:
   transferring the one or more droplets between a plurality of reservoir electrodes using droplet operations along a loop of the pathway; and
   transferring the one or more droplets from the loop to the outlet electrodes using droplet operations along a snaking path of the pathway.

18. The method of claim 16 wherein the reservoir electrode is one of a plurality of reservoir electrodes arranged radially with respect to the outlet electrodes, and wherein each of the plurality of reservoir electrodes is connected to a dedicated arrangement of the droplet operations electrodes.

19. The method of claim 16 wherein the one or more droplets are transferred to the flow cell in a predetermined sequence for performing sequencing-by-synthesis reactions.

20. A digital microfluidic liquid handling system for supplying liquids to a flow cell, comprising:

a processor for executing code and a memory in communication with the processor, the system comprising code stored in the memory that causes the processor at least to:

dispense one or more droplets from a liquid reservoir onto a reservoir electrode corresponding with the liquid reservoir, the reservoir electrode being positioned in a droplet operations gap of a droplet actuator including a top substrate and a bottom substrate separated to form the droplet operations gap, wherein the top substrate includes an opening;

fill the droplet operations gap of the droplet actuator with a filler fluid;

transfer the one or more droplets from the reservoir electrode to outlet electrodes along a pathway defined by droplet operations electrodes;

transfer the one or more droplets from the outlet electrodes through the opening arranged proximal thereto and into a flow cell in a predetermined sequence;

monitor an impedance at the outlet electrodes during flow of the one or more droplets;

detect a change in the impedance in response to the transfer of the one or more droplets from the outlet electrodes; and in response to the detection, stop a pump used to transfer the one or more droplets from the outlet electrodes until additional droplets are pooled at the outlet electrodes.

* * * * *